(12) United States Patent
Palombella et al.

(10) Patent No.: US 6,660,268 B1
(45) Date of Patent: *Dec. 9, 2003

(54) PROTEASOME REGULATION OF NF-KB ACTIVITY

(75) Inventors: Vito J. Palombella, Needham, MA (US); Alfred L. Goldberg, Brookline, MA (US); Thomas P. Maniatis, Belmont, MA (US); Oliver Rando, Newton, MA (US)

(73) Assignee: The President and Fellows of Harvard College, Cambridge, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/210,381

(22) Filed: Mar. 18, 1994

(51) Int. Cl.$^7$ .................. A61K 39/00; A61K 39/38; A61K 31/00; A01N 61/00

(52) U.S. Cl. ................. 424/184.1; 514/1; 514/2

(58) Field of Search ................ 514/18, 1, 2; 424/184.1

(56) References Cited

U.S. PATENT DOCUMENTS

| | | |
|---|---|---|
| 4,510,130 A | 4/1985 | Platt et al. |
| 5,693,617 A * | 12/1997 | Stein et al. |
| 6,410,516 B1 | 6/2002 | Baltimore et al. |

FOREIGN PATENT DOCUMENTS

| | | |
|---|---|---|
| EP | 363284 | 4/1990 |
| EP | 364344 | 4/1990 |
| EP | 393457 | 10/1990 |
| EP | 0 407 411 B1 | 11/1993 |
| WO | WO 88/10266 | 12/1988 |
| WO | WO A 89 08147 | 9/1989 |
| WO | WO 91/13904 | 9/1991 |
| WO | WO 92/11850 | 7/1992 |
| WO | WO 92/12140 | 7/1992 |
| WO | WO A 92 20795 | 11/1992 |
| WO | WO 94/23045 | 10/1994 |

OTHER PUBLICATIONS

Oberg et al (Eur. J. Clin. Microbiol. Inf. Dis. vol. 9(7) pp. 466–471), Jul. 1990.*
Gait et al (TIBTECH vol. 13 pp. 430–438), 1995.*
Flexner et al (*AIDS, Biology, Diagnosis, Treatment & Prevention* pp. 479–493), 1997.*
Sandstrom et al (Bioessays vol. 18 No. 5, pp. 343–346), 1996.*
Bilbao et al (British Journal of Radiology Mar. 1992 65(771) pp. 248–251).*
Isoe et al (Anticancer Research Sep.–Oct. 1991, 11(5) pp. 1905–1909).*
Divarello et al (J. of Immunology Sep. 1984 133(3) pp. 1332–1338) *Current Surgical Diagnosis of Treatment* Edward B. Way, Ninth Edition, Large Medical Publications, 1991 pp. 95–96, and 622).*
Bendtzev (Immunology Letters vol. 19, 1988 pp. 183–192).*
Djaballah et al., Am. J. Biochem. 209:629–634, 1992.
Guesdon et al., Biochem. J. 307:287–295, 1995.
Hough et al., J. Biol. Chem. 262:8303–8309, 1987.
Sodhi, Ajit et al., "Mechanism of NF–κB translocation in macrophages treated in vitro with cisplatin", Immunology Letters 63 (1998), pp. 9–17.
Das, Kumuda C. et al., "Activation of NKF–κB by Antineoplastic Agents/Role of Protein Kinase C", The Journal of Biological Chemistry, vol. 272, No. 23 (1997), pp. 14914–14920.
Palombella et al. (1994) Cell 78:773–785.
Traenckner et al. (1994) EMBO J. 13:5433–5411.
Finco et al. (1994) Proc Nat'l. Acad. Sci. USA 91:11884–11888.
Miyamoto et al. (1994) Proc. Nat'l. Acad. Sci. USA 91:12740–12744.
Lin et al. (1995) Proc. Nat'l. Acad. Sci. USA 92:552–556.
Alkalya et al. (1995) Mol. Cell. Biol. 15:1294–1301.
DiDonato et al. (1995) Mol. Cell Biol. 15:1302–1311.
Schreck et al. (1992) Journal of Experimental Medicine 175:1181–1194.
Vinitsky et al. Biochemistry (1992) 31:9421–9428.
R. Sen et al. (1986) Cell 47:921–928.
R. Wall et al. (1986) Proc. Nat'l. Acad. Sci. USA 83:295–298.
P. A. Baeuerle et al. (1988) Cell 53:211–217.
S. Haskill et al. (1991) Cell 65:1281–1289.
S. Ghosh et al. (1990) Nature 344:678–682.
U. Zabel et al. (1990) Cell 61:255–265.
S. Miyamoto et al. Chemical Abstracts, Jul. 4, 1994, vol. 121 No. 1 Columbus, Ohio, USA.
T. Machleidt et al. Chemical Abstracts, Jun. 20, 1994, vol. 120 No. 25 Columbus, Ohio, USA.
S. Jentsch et al. Cell 82:881–884 (1995).
W. Sha et al. Cell 80:321–330 (1995).
Goldberg Eur. J. Biochem 203:9–23 (1992).
Angelastro et al., "α–Diketone and α–Keto Ester Derivatives of N–Protected Amino Acids and Peptides as Novel Inhibitors of Cysteine and Serine Proteinases," *J. Med. Chem.* 33:11–13 (1990).
Angliker et al., "The synthesis of lysylfluoromethanes and their properties as inhibitors of trypsin, plasmin and cathepsin B," *Biochem. J.* 241:871–875 (1987).

(List continued on next page.)

Primary Examiner—Mark Navarro
(74) Attorney, Agent, or Firm—Hale and Dorr LLP

(57) ABSTRACT

Disclosed herein is a method for regulating the activity of NF-κB in an animal comprising contacting cells of the animal with certain proteasome inhibitors.

3 Claims, 11 Drawing Sheets

OTHER PUBLICATIONS

Aoyagi & Umezawa, "Structures and Activities of Protease Inhibitors of Microbial Origin," *Proteases and Biol. Control,* Cold Spring Harbor Press, pp. 429–454 (1975).

Bachmair, et al., "In Vivo Half–Life of a Protein Is a Function of Its Amino–Terminal Residue," *Science 234:*179–186 (Oct. 10, 1986).

Badalamente et al., "Neuromuscular recovery using calcium protease inhibition after median nerve repair in primates," *Proc. Natl. Acad. Sci. U.S.A. 86:*5983–5987 (Aug., 1989).

Beg & Baldwin, The IκB proteins: multifunctional regulators of Rel/NF–κB transcription factors, *Genes & Development 7:*2064–2070 (1993).

Beg et al., "Tumor Necrosis Factor and Interleukin–1 Lead to Phosphorylation and Loss of IκBα: a Mechanism for NF–κB Activation," *Molecular and Cellular Biology 13(6):*3301–3310 (Jun. 1993).

Boches & Goldberg, "Role for the Adenosine Triphosphate–Dependent Proteolytic Pathway in Reticulocyte Maturation," *Science 215:*978–980 (Feb. 19, 1982).

Bours et al., "A Novel Mitogen–Inducible Gene Product Related to p50/p105–NF–κB Participates in Transactivation through a κB Site," *Molecular and Cellular Biology 12:*685–695 (Feb. 1992).

Brown et al., "Structural and serological similarity of MHC–linked LMP and proteasome (multicatalytic proteinase) complexes," *Nature 353:*355–357 (Sep. 26, 1991).

Ciechanover et al., "Ubiquitin Dependence of Selective Protein Degradation Demonstrated in the Mammalian Cell Cycle Mutant ts85," *Cell 37:*57–66 (May 1984).

Dick et al., "Degradation of Oxidized Insulin B Chain by the Multiproteinase Complex Macropain (Proteasome)," *Biochemistry 30:*2725–2734 (1991).

Driscoll & Finley, "A Controlled Breakdown: Antigen Processing and the Turnover of Viral Proteins," *Cell 68:*823–825 (Mar. 6, 1992).

Driscoll & Goldberg, "The Proteasome (Multicatalytic Protease) Is a Component of the 1500–kDa Proteolytic Complex Which Degrades Ubiquitin–conjugated Proteins," *J. Biol. Chem. 265:*4789–4792 (Mar. 25, 1990).

Ewoldt et al., "Sulfonyl Fluoride Serine Protease Inhibitors Inactivate RNK–16 Lymphocyte Granule Proteases and Reduce Lysis by Granule Extracts and Perforin," *Mol. Imm. 29:*713–721 (1992).

Eytan et al., "ATP–dependent incorporation of 20S protease into the 26S complex that degrades proteins conjugated to ubiquitin," *Proc. Natl. Acad. Sci. USA 86:*7751–7755 (Oct. 1989).

Fan & Maniatis, "Generation of p50 subunit of NF–κB by processing of p105 through an ATP–dependent pathway," *Nature 354:*395–398 (Dec. 1991).

Fehrentz et al., "Synthesis of aldehydic peptides inhibiting renin," *Int. J. Peptide Protein Res. 26:*236–241 (1985).

Fehrentz & Castro, "An Efficient Synthesis of Optically Active α–(t–Butoxycarbonylamino)–aldehydes from α–Amino Acids," *Synthesis* pp. 676–678 (1983).

Ganoth et al., "A Multicomponent System That Degrades Protein Conjugated to Ubiquitin," *J. Biol. Chem. 263:*12412–12419 (Sep. 5, 1988).

Glynne et al., "A proteasome–related gene between the two ABC transporter loci in the class II region of the human MHC," *Nature 353:*357–360 (Sep. 26, 1991).

Goldberg, A., "The mechanism and functions of ATP–dependent proteases in bacterial and animal cells," *Eur. J. Biochem. 203:*9–23 (1992).

Goldberg & Rock, "Proteolysis, proteasomes and antigen presentation," *Nature 357:*375–379 (Jun. 4, 1992).

Gonda, et al., "Universality and Structure of the N–end Rule," *J. Biol. Chem. 264:*16700–16712 (Oct. 5, 1989).

Green & Shaw, "Peptidyl Diazomethyl Ketones Are Specific Inactivtors of Thiol Proteinases," *J. Biol. Chem. 256:*1923–1928 (Feb. 25, 1981).

Grilli et al., "NF–κB and Rel: Participants in a Multiform Transcriptional Regulatory System," *International Rev. of Cytol. 143:*1–62 (1993).

Gronostajski et al., "The ATP Dependence of the Degradation of Short– and Long–lived Proteins in Growing Fibroblasts," *J. Biol. Chem. 260:*3344–3349 (Mar. 25, 1985).

Hanada et al., "Characterization of the Three New Analogs of E–64 and Their Therapeutic Application," in: *Proteinase Inhibitors: Medical and Biological Aspects,* Katunuma et al., Eds., Springer–Verlag pp. 25–36 (1983).

Henkel et al., "Rapid proteolysis of IκB–α is necessary for activation of transcription factor NF–κB," *Nature 365:*182–185 (Sep. 9, 1993).

Hernandez et al., "Effect of the 7–Amino Substituent on the Inhibitory Potency of Mechanism–Based Isocoumarin Inhibitors for Porcine Pancreatic and Human Neutrophil Elastases," *J. Med. Chem. 35:*1121–1129 (1992).

Hershko & Ciechanover, "The Ubiquitin System for Protein Degradation," *Ann. Rev. Biochem. 61:*761–807 (1992).

Hough et al., "Purification of Two High Molecular Weight Proteases from Rabbit Reticulocyte Lysate," *Biochem. 262:*8303–8313 (Jun. 15, 1987).

Hudig et al., "Selective Isocoumarin Serine Protease Inhibitors Block RNK–16 Lymphocyte Granule–Mediated Cytolysis," Molecular *Immunology 26:*793–798 (1989).

Kam et al., "Mechanism–Based Isocoumarin Inhibitors for Trypsin and Blood Coagulation Serine Proteases: New Antigoagulatns," *Biochemistry 27:*2547–2557 (1988).

Kelly et al., "Second proteasome–related gene in the human MHC class II region," *Nature 353:*667–668 (Oct. 1991).

Kennedy & Schultz, "Mechanism of Association of a Specific Aldehyde 'Transition–State Analogue' to the Active Site of α–Chymotrypsin," *Biochem. 18:*349–356 (1979).

Hudig et al., "Inhibition and Restoration of Granule–Mediated Lysis with Isocoumarin Serine Protease Inhibitors," *J. Immunol. 147:*1360–1368 (Aug. 15, 1991).

Kajiwara et al., "Elucidation of Calpain Dependent Phosphorylation of Myosin Light Chain in Human Platelets," *Biochem. Int. 15:*935–944 (Nov. 1987).

Kam et al., "Thioester Chromogenic Substrates for Human Factor VIIa: Substituted Isocoumarins Are Inhibitors of Factor VIIa and In Vitro Anticoagulants," *Thrombosis & Haemostasis 64:*133–137 (1990).

Li et al., "Isolation and Characterization of a Novel Endogenous Inhibitor of the Proteasome," *Biochem. 30:*9709–9715 (1991).

Martinez & Monaco, "Homology of proteasome subunits to a major histocompatibility complex–linked LMP gene," *Nature 353:*664–667 (Oct. 17, 1991).

Matthews et al., "Involvement of the proteasome in various degradative processes in mammalian cells," *Proc. Natl. Acad. Sci. USA 86:*2597–2601 (Apr. 1989).

McGuire et al., "An enzyme related to the high molecular weight multicatalytic proteinase, macropain, participates in a ubiquitin–mediated, ATP–stimulated proteolytic pathway in soluble extracts of BHK 21/C13 fibroblasts," *Biochim. Biophys. Acta 967:*195–203 (1988).

Mellits et al., "Proteolytic degradation of MAD3 (IκBα) and enhanced processing of the NF–κB precursor p105 are obligatory steps in the activation of NF–κB," *Nucleic Acids Research 21:*5059–5066 (1993).

Mercurio et al., "Molecular Cloning and Characterization of a Novel Rel/NF–κB Family Member Displaying Structural and Functional Homology to NF–κ p50/p105," *DNA and Cell Biology 11:*523–537 (1992).

Michalek et al., "A role for the ubiquitin–dependent proteolytic pathway in MHC class I–restricted antigen presentation," *Nature 363:*552–554 (Jun. 10, 1993).

Monaco, J., "A molecular model of MHC class–I–restricted antigen processing," *Immun. Today 13:*173–179 (1992).

Monaco & McDevitt, "The LMP Antigens: A Stable MHC–Controlled Multisubunit Protein Complex," *Human Imm. 15:*416–426 (1986).

Monaco & Mc Devitt, "Identification of a fourth class of proteins linked to the murine major histocompatibility complex," *Proc. Natl. Acad. Sci. USA 79:*3001–3005 (May 1982).

Moore et al., "Introduction of Soluble Protein into the Class I Pathway of Antigen Processing and Presentation," *Cell 54:*777–785 (Sep. 9, 1988).

Morrison et al., "Differences in Antigen Presentation to MHC Class I– and Class II–Restricted Influenza Virus–Specific Cytolytic T Lymphocyte Clones," *J. Exp. Med. 163:*903–921 (Apr. 1986).

Murakami & Ettinger, "Endogenous inhibitor of nonlysosomal high molecular weight protease and calcium–dependent protease," *Proc. Natl. Acad. Sci. USA 83:*7588–7592 (Oct. 1986).

Neri et al., "B Cell Lymphoma–Associated Chromosomal Transloaction Involves Candidate Oncogene lyt–10, Homologous to NF–κB p50," *Cell 67:*1075–1087 (Dec. 20, 1991).

Odake et al., "Human and Murine Cytotoxic T Lymphocyte Serine Proteases: Subsite Mapping with Peptide Thioester Substrates and Inhibition of Enzyme Activity and Cytolysis by Isocoumarins," *Biochem. 30:*2217–2227 (1991).

Ortiz–Navarrete et al., "Subunit of the '20S' proteasome (multicatalytic proteinase) encoded by the major histocompatibility complex," *Nature 353:*662–664 (Oct. 17, 1991).

Orlowski, M., "The Multicatalytic Proteinase Complex, a Major Extralysosomal Proteolytic System," *Biochemistry 29:*10289–10297 (Nov. 13, 1990).

Orlowski et al., "Substrate Specificity and Inhibitors of a Capillary Injury–Related Protease from Sheep Lung Lymph," *Arch. Biochem. & Biophys. 269:*125–136 (Feb. 15, 1989).

Orlowski et al., "Evidence for the Presence of Five Distinct Proteolytic Components in the Pituitary Multicatalytic Proteinase Complex. Properties of Two Components Cleaving Bonds on the Carboxyl Side of Branched Chain and Small Neutral Amino Acids," *Biochemistry 32:*1563–1572 (1993).

Oweida et al., "In Vivo Determination of the Anticoagulant Effect of a Substituted Isocoumarin (Acitic)," *Thrombosis Research 58:*191–197 (1990).

Parham, P., "Transporters of delight," *Nature 348:*674–675 (Dec. 17, 1990).

Parkes et al., "Calpain inhibition by peptide epoxides," *Biochem J. 230:*509–516 (1985).

Powers & Harper, "Inhibitors of serine proteinases," in: *Proteinase Inhibitors,* Barrett et al. (eds.), Elsevier, pp. 55–152 (1986).

Powers et al., "Reaction of Porcine Pancreatic Elastase with 7–Subsituted 3–Alkoxy–4–chloroisocoumarins: Design of Potent Inhibitors Using the Crystal Structure of the Complex Formed with 4–Chloro–3–ethoxy–7–guanidinoisocoumarin," *Biochemistry 29:*3108–3118 (1990).

Powers et al., "Mechanism–Based Isocoumarin Inhibitors for Serine Proteases: Use of Active Site Structure and Substrate Specificity in Inhibitor Design," *Journal of Cellular Biochemistry 39:*33–46 (1989).

Powis et al., "Restoration of antigen presentation to the mutant cell line RMA–S by an MHC–linked transporter," *Nature 354:*528–531 (Dec. 26, 1991).

Puri et al., "Thrombin–Induced Platelet Aggregation Involves an Indirect Proteolytic Cleavage of Aggregin by Calpain," *Arch. Biochem. Biophys. 271:*346–358 (Jun. 1989).

Rao et al., "Influence of a Calcium Dependent Protease Inhibitor on Platelet Activation and Secretion," *Thromb. Res. 47:*625–637 (1987).

Rechsteiner, M., "Ubiquitin–Mediated Pathways for Intracellular Proteolysis," *Ann. Rev. Cell. Biol. 3:*1–30 (1987).

Rivett, A., "The Multicatalytic Proteinase," *J. Biol. Chem. 264:*12215–12219 (Jul. 25, 1989).

Rivett et al., "The Multicatalytic Proteinase of Mammalian Cells," *Arch. Biochem. Biophys. 268:*1–8 (Jan. 1989).

Schmid et al., "Cloning of an NF–κB subunit which stimulates HIV transcription in synergy with p65," *Nature 352:*733–736 (Aug. 22, 1991).

Sheehan et al., "A Rapid Synthesis of Oligopeptide Derivatives without Isolation of Intermediates," *J. Am. Chem. Soc. 87:*2492–2493 (Jun. 5, 1965).

Speiser & Etlinger, "Loss of ATP–dependent Proteolysis with Maturation of Reticulocytes and Erythrocytes," *J. Biol. Chem. 257:*14122–14127 (Dec. 10, 1982).

Spies & DeMars, "Restored expression of major histocompatibility class I molecules by gene transfer of a putative peptide transporter," *Nature 351:*323–324 (May 23, 1991).

Staubli et al., "Chronic administration of a thiol–proteinase inhibitor blocks long–term potentiation of synaptic responses," *Brain Research 444:*153–158 (1988).

Tanaka et al., "Proteasomes: Protein and Gene Structures," *New Biol. 4:*173–187 (Mar. 1992).

Townsend et al., "Cytotoxic T Cells Recognize Fragments of the Influenza Nucleoprotein," *Cell 42:*457–467 (Sep. 1985).

Townsend et al., "Cytotoxic T lymphocytes recognize influenza haemagglutinin that lacks a signal sequence," *Nature 324:*575–577 (Dec. 11, 1986).

Townsend et al., "Defective Presentation to Class I–Restricted Cytotoxic T Lymphocytes in Vaccinia–Infected Cells in Overcome by Enhanced Degradation of Antigen," *J. Exp. Med. 168:*1211–1224 (Oct. 1988).

Tsubuki et al., "Purification and Characterization of A Z–Leu–Leu–MCA Degrading Protease Expected to Regulate Neurite Formation: A Novel Catalytic Activity in Proteasome," *Biochem. and Biophys. Res. Commun. 196(3):*1195–1201 (Nov. 15, 1993).

Tsujinaka et al., "Synthesis of a New Cell Penetrating Calpain Inhibitor (Calpeptin)," *Biochem. Biophys. Res. Commun. 153:*1201–1208 (Jun. 30, 1988).

Vijayalakshmi et al., "Structural Study of Porcine Pancreatic Elastase Complexed with 7–Amino–3–(2–bromoethoxy)–4–chloroisocoumarin as a Nonreactivatable Doubly Covalent Enzyme–Inhibitor Complex," *Biochem. 30:*2175–2183 (1991).

Vinitsky et al., "Inhibition of the Chymotrypsin–like Activity of the Pituitary Multicatalytic Proteinase Complex," *Biochemistry 31:*9421–9428 (1992).

Vlasak et al., "Influenze C Virus Esterase: Analysis of Catalytic Site, Inhibition, and Possible Function," *J. Virol. 63:*2056–2062 (May 1989).

Waxman et al., "Demonstration of Two Distinct High Molecular Wieght Proteases in Rabbit Reticulocytes, One of Which Degrades Ubiquitin Conjugates," *J. Biol. Chem. 262:*2451–2457 (Feb. 25, 1987).

Wilkinson et al., "A Specific Inhibitor of the Ubiquitin Activating Enzyme: Synthesis and Characterization of Adenosyl–Phospho–Ubiquitinol, a Nonhydrolyzable Ubiquitin Adenylate Analogue," *Biochemistry 29:*7373–7380 (1990).

Yang et al., "Proteasomes are regulated by interferon γ: Implications for antigen processing," *Proc. Natl. Acad. Sci. USA 89:*4928–4932 (Jun. 1992).

Yewdell & Bennink, "Cell Biology of Antigen Processing and Presentation to Major Histocompatibility Complex Class I Molecule–Restricted T Lymphocytes," *Adv. Immun. 52:*1–123 (1992).

Zunino et al., "Localization, implications for function, ang gene expression of chymotrypsin–like proteinases of cytotoxic RNK–16 lymphocytes," *Biochimica et Biophysica Acta. 967:*331–340 (1988).

\* cited by examiner

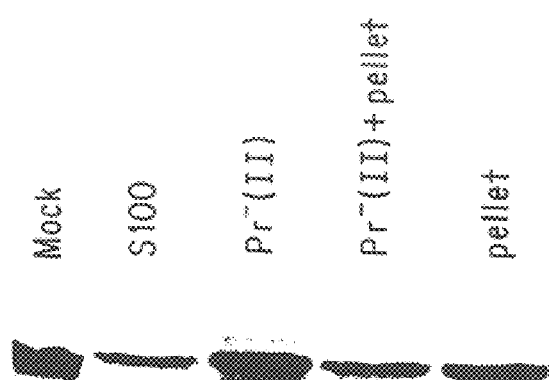
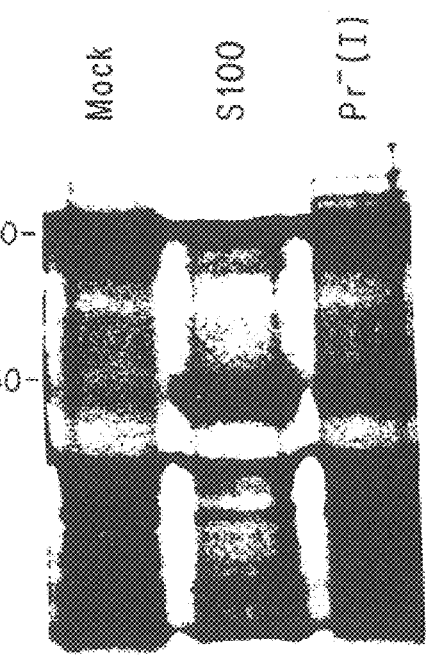
α-p50
FIG. 3A
α-myc 9E10
FIG. 3B

PROTEASOME REGULATION OF NF-κB ACTIVITY

The U.S. government has a paid-up license in this invention and the right in limited circumstances to require the patent owner to license others on reasonable terms as provided for by the terms of Grant Numbers RO1-GM 46147-02 and R37 AI20642 awarded by the NIH/National Institute of General Medical Sciences and NIH/NIAID, respectively.

BACKGROUND OF THE INVENTION

1. Field of the Invention

The present invention relates to a method for reducing the cellular content and activity of NF-κB by use of inhibitors of proteasome function or ubiquitin conjugation.

2. Description of Related Art

The transcription factor NF-κB and other members of the rel family of protein complexes play a central role in the regulation of a remarkably diverse set of genes involved in the immune and inflammatory responses (Grilli et al., *International Review of Cytology* 143:1–62 (1993)). For example, NF-κB is required for the expression of a number of immune response genes, including the Ig-κ light chain immunoglobulin gene, the IL-2 receptor α chain gene, the T cell receptor β chain gene, and class I and II major histocompatibility genes. In addition, NF-κB has been shown to be required for a number of genes involved in the inflammatory response, such as the TNF-α gene and the cell adhesion genes, E-selectin, I-cam, and V-cam. NF-κB is also required for the expression of a large number of cytokine genes such as IL-2, IL-6, G-CSF, and IFN-β. Finally, NF-κB is essential for the expression of the human immunodeficiency virus (HIV).

In the cytosol, there is a soluble proteolytic pathway that requires ATP and involves covalent conjugation of the cellular proteins with the small polypeptide ubiquitin ("Ub") (Hershko et al., *A. Rev. Biochem.* 61:761–807 (1992); Rechsteiner et al., *A. Rev. Cell. Biol.* 3:1–30 (1987)). Thereafter, the conjugated proteins are hydrolyzed by a 26S proteolytic complex containing a 20S degradative particle called the proteasome (Goldberg, *Eur. J. Biochem.* 203:9–23 (1992); Goldberg et al., *Nature* 357:375–379 (1992)). This multicomponent system is known to catalyze the selective degradation of highly abnormal proteins and short-lived regulatory proteins. However, the system also appears to be responsible for the breakdown of most proteins in maturing reticulocytes (Boches et al., *Science* 215:978–980 (1982); Spenser et al., *J. Biol. Chem.* 257:14122–14127 (1985)), in growing fibroblasts (Ciechanover et al., *Cell* 37:57–66 (1984); Gronostajski et al., *J. Biol. Chem.* 260:3344–3349 (1985)), and in atrophying skeletal muscle.

The first step in degradation of many proteins involves their conjugation to Ub by an ATP-requiring process. The ubiquitinated proteins are then degraded by an ATP-dependent proteolytic complex, referred to above, known as the 26S proteasome complex.

The precise nature of the 26S proteasome complex is unclear, although it has been shown that the 1000–1500 kDa (26S) complex can be formed in extracts of energy-depleted reticulocytes by an ATP-dependent association of three components, referred to as CF-1, CF-2, and CF-3 (Ganoth, D. et al., *J. Biol. Chem.* 263:12412–12419 (1988)). A large (~700 kDa) multimeric protease found in the cytoplasm and nucleus of eukaryotic cells, referred to as the proteasome, is a component (CF-3) (Driscoll et al., *J. Biol. Chem.* 265:4789–4792 (1992); Eytan et al., *Proc. Natl. Acad. Sci. USA* 86:7751–7755 (1989); Orlowski, *Biochemistry* 29:10289–10297 (1990) and Rivett, *Arch. Biochem. Biophys.* 268:1–8 (1989)).

The proteasome is believed to make up the catalytic core of the large 26S multisubunit cytoplasmic particle necessary for the ubiquitin-dependent pathway of intracellular proteolysis (Driscoll et al., *J. Biol. Chem.* 265:4789–4692 (1990); Eytan et al., *Proc. Natl. Acad. Sci. U.S.A.* 86:7751–7755 (1989); Hough et al., *Biochemistry* 262:8303–8313 (1987); McGuire et al., *Biochim. Biophys. Acta* 967:195–203 (1988); Rechsteiner et al., *A. Rev. Cell. Biol.* 3:1–30 (1987); Waxman et al., *J. Biol. Chem.* 262:2451–2457 (1987)). By itself, the proteasome is unable to degrade ubiquitinated proteins, but provides most of the proteolytic activity of the 26S proteasome complex.

There is another ATP-dependent protease that is involved in degradation of ubiquitinated proteins, forms a complex with the proteasome, and appears to be part of the 26S proteasome complex, which rapidly degrades proteins conjugated to ubiquitin. This protease, referred to as multipain, has been identified in muscle and plays an essential role in the ATP-ubiquitin-dependent pathway.

The complex formed between multipain and proteasome in vitro appears very similar or identical to the 1500 kDa Ub-conjugate, degrading enzyme, or 26S proteolytic complex, isolated from reticulocytes and muscle. The complexes contain the characteristic 20–30 kDa proteasome subunits, plus a number of larger subunits, including the six large polypeptides found in multipain. The complex formed contains at least 10–12 polypeptides of 40–150 kDa.

A 40 kDa polypeptide regulator of the proteasome, which inhibits the proteasome's proteolytic activities has been purified from reticulocytes and shown to be an ATP-binding protein whose release appears to activate proteolysis. The isolated regulator exists as a 250 kDa multimer and is quite labile (at 42° C.). It can be stabilized by the addition of ATP or a nonhydrolyzable ATP analog, although the purified regulator does not require ATP to inhibit proteasome function and lacks ATPase activity. The regulator has been shown to correspond to an essential component of the 1500 kDa proteolytic complex. The regulator appears identical to CF-2 by many criteria. These findings suggest that the regulator plays a role in the ATP-dependent mechanism of the 26S proteasome complex.

There is also a system in the cytosol that generates antigenic particles from endogenously synthesized cellular and viral proteins (Moore et al., *Cell* 54:777–785 (1988); Morrison et al., *J. Exp. Med.* 163:903–921 (1986); Powis et al., *Nature* 354:529–531 (1991); Spies et al., *Nature* 351:323–324 (1991); Townsend et al., *Cell* 42:457–467 (1985); Townsend et al., *Nature* 324:575–577 (1986); Monaco et al., *Proc. Natl. Acad. Sci. U.S.A.* 79:3001–3005 (1982); Monaco, *Immun. Today* 13:173–179 (1992); Yewdell et al., *Adv. Immun.* 52:1–123 (1992); Townsend et al., *J. Exp. Med.* 168:1211–1224 (1988)). Indirect evidence suggests a role for proteolytic particles closely resembling and perhaps identical to the proteasome (Goldberg et al., *Nature* 357:375–379 (1992); Monaco, *Immun. Today* 13:173–179 (1992); Parham, *Nature* 348:674–675 (1990); Yang et al., *Proc. Natl. Acad. Sci. U.S.A.* 89:4928–4932 (1992); (Brown et al., *Nature* 353:355–357 (1991)). It has been shown that the proteasome is responsible for cytoplasmic processing of MHC class I antigen molecules.

The 20S proteasome is composed of about 15 distinct 20–30 kDa subunits. It contains at least three different peptidases that cleave specifically on the carboxyl side of the hydrophobic, basic, and acidic amino acids (Goldberg et al., *Nature* 357:375–379 (1992); Goldberg, *Eur. J. Biochem.* 203:9–23 (1992); Orlowski, *Biochemistry* 29:10289–10297 (1990); Rivett et al., *Archs. Biochem. Biophys.* 218:1 (1989); Rivett et al., *J. Biol. Chem.* 264:12,215–12,219 (1989); Tanaka et al., *New Biol.* 4:1–11 (1992)). These peptidases are referred to as the chymotrypsin-like peptidase, the trypsin-like peptidase, and the peptidylglutamyl peptidase. Which subunits are responsible for these activities is unknown, although the cDNA's encoding several subunits have been cloned (Tanaka et al., *New Biol.* 4:1–11 (1992)).

Recent studies have found that the 20S proteasomes resemble in size and subunit composition the MHC-linked LMP particles (Driscoll et al., *Cell* 68:823 (1992); Goldberg et al., *Nature* 357:375–379 (1992); Matthews et al., *Proc. Natl. Acad. Sci. U.S.A.* 86:2586 (1989); Monaco et al., *Human Immunology* 15:416 (1986); Parham, *Nature* 348:674–675 (1990); Martinez et al., *Nature* 353:664 (1991); Oritz-Navarette et al., *Nature* 353:662 (1991); Glynne et al., *Nature* 353:357 (1991); Kelly et al., *Nature* 353:667 (1991); Monaco et al., *Proc. Natl. Acad. Sci. U.S.A.* 79:3001 (1982); Brown et al., *Nature* 353:355 (1991); Goldberg, *Eur. J. Biochem.* 203:9–23 (1992); Tanaka et al., *New Biol.* 4:1–11 (1992)).

Various inhibitors of the peptidases of the proteasome have been reported (Dick et al., *Biochemistry* 30:2725–2734 (1991); Goldberg et al., *Nature* 357:375–379 (1992); Goldberg, *Eur. J. Biochem.* 203:9–23 (1992); Orlowski, *Biochemistry* 29:10289–10297 (1990); Rivett et al., *Archs. Biochem. Biophys.* 218:1 (1989); Rivett et al., *J. Biol. Chem.* 264:12,215–12,219 (1989); Tanaka et al., *New Biol.* 4:1–11 (1992)). These include known inhibitors of chymotrypsin-like and trypsin-like proteases, as well as inhibitors of thiol (or cysteine) and serine proteases. In addition, some endogenous inhibitors of proteasome activities have been isolated. These include the 240 kDa and the 200 kDa inhibitors isolated from human erythrocytes (Murakami et al., *Proc. Natl. Acad. Sci. U.S.A.* 83:7588–7592 (1986); Li et al., *Biochemistry* 30:9709–9715 (1991)) and purified CF-2 (Goldberg, *Eur. J. Biochem.* 203:9–23 (1992)). In addition to antibiotic inhibitors originally isolated from actinomycetes (Aoyagi et al., *Proteases and Biological Control*, Cold Spring Harbor Laboratory Press, pp. 429–454 (1975)), a variety of peptide aldehydes have been synthesized, such as the inhibitors of chymotrypsin-like proteases described by Siman et al. (WO 91/13904).

Novel molecules can also be obtained and tested for inhibitory activity. As illustrated by the above cited references, various strategies are known in the art for obtaining the inhibitors for a given protease. Compound or extract libraries can be screened for inhibitors using peptidase assays. Alternatively, peptide and peptidomimetic molecules can be designed based on knowledge of the substrates of the protease. For example, substrate analogs can be synthesized containing a reactive group likely to interact with the catalytic site of the protease (see, e.g., Siman et al., WO 91/13904; Powers et al., in *Proteinase Inhibitors*, Barrett et al. (eds.), Elsevier, pp. 55–152 (1986)). The inhibitors can be stable analogs of catalytic transition states (transition state analog inhibitors), such as Z-Gly-Gly-Leu-H, which inhibits the chymotrypsin-like activity of the proteasome (Orlowski, *Biochemistry* 29:10289–10297 (1990); see also Kennedy and Schultz, *Biochemistry* 18:349 (1979)).

Various natural and chemical protease inhibitors reported in the literature, or molecules similar to them, include peptides containing an α-diketone or an α-keto ester, peptide chloromethyl ketones, isocoumarins, peptide sulfonyl fluorides, peptidyl boronates, peptide epoxides, and peptidyl diazomethanes (Angelastro et al., *J. Med Chem.* 33:11–13 (1990); Bey et al., EPO 363,284; Bey et al., EPO 364,344; Grubb et al., WO 88/10266; Higuchi et al., EPO 393,457; Ewoldt et al., *Molecular Immunology* 29(6):713–721 (1992); Hernandez et al., *Journal of Medicinal Chemistry* 35(6): 1121–1129 (1992); Vlasak et al., *Journal of Virology* 63(5):2056–2062 (1989); Hudig et al., *Journal of Immunology* 147(4): 1360–1368 (1991); Odake et al., *Biochemistry* 30(8):2217–2227 (1991); Vijayalakshmi et al., *Biochemistry* 30(8):2175–2183 (1991); Kam et al., *Thrombosis and Haemostasis* 64(1):133–137 (1990); Powers et al., *Journal of Cellular Biochemistry* 39(1):33–46 (1989); Powers et al., *Proteinase Inhibitors*, Barrett et al., Eds., Elsevier, pp. 55–152 (1986); Powers et al., *Biochemistry* 29(12):3108–3118 (1990); Oweida et al., *Thrombosis Research* 58(2):391–397 (1990); Hudig et al., *Molecular Immunology* 26(8):793–798 (1989); Orlowski et al., *Archives of Biochemistry and Biophysics* 269(1): 125–136 (1989); Zunino et al., *Biochimica et Biophysica Acta.* 967(3):331–340 (1988); Kam et al., *Biochemistry* 27(7):2547–2557 (1988); Parkes et al., *Biochem J.* 230:509–516 (1985); Green et al., *J. Biol. Chem.* 256:1923–1928 (1981); Angliker et al., *Biochem. J.* 241:871–875 (1987); Puri et al., *Arch. Biochem. Biophys.* 27:346–358 (1989); Hanada et al., *Proteinase Inhibitors: Medical and Biological Aspects*, Katunuma et al., Eds., Springer-Verlag pp. 25–36 (1983); Kajiwara et al., *Biochem. Int.* 15:935–944 (1987); Rao et al., *Thromb. Res.* 47:635–637 (1987); Tsujinaka et al., *Biochem. Biophys. Res. Commun.* 153:1201–1208 (1988)).

Various inhibitors of ubiquitin conjugation to proteins are also known (Wilkinson et al., *Biochemistry* 29:7373–7380 (1990)).

Certain peptide aldehydes and peptide α-keto esters containing a hydrophobic residue in the $P_1$ position were tested by Vinitsky et al. (*Biochemistry* 31:9421–9428 (1992), see also, Orlowski et al. *Biochemistry* 32:1563–1572 (1993)) as potential inhibitors of the chymotrypsin-like activity of the proteasome. Three peptide aldehydes, (benzyloxycarbonyl)-Leu-Leu-phenylalaninal (Z-LLF-H), N-acetyl-Leu-Leu-Norleucinal (Ac-LLnL-H), and N-acetyl-Leu-Leu-methioninal (Ac-LLM-H) were found to be slow binding inhibitors with $K_i$ values of 0.46, 5.7, and 33 µM, respectively. Of the several peptide α-keto ester inhibitors tested, Z-Leu-Leu-Phe-COOEt was the most potent inhibitor of the chymotrypsin-like activity with a $K_i$ of 53 µM. Many such compounds exist.

Other tripeptides that have been described in the literature include Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H, and Z-Arg-Ile-Phe-H, where OR, along with the carbonyl of the preceding amino acid residue, represents an ester group.

Goldberg, in U.S. patent application Ser. No. 07/699,184, filed May 13, 1991, now U.S. Pat. No. 5,340,736 discloses that the ATP-ubiquitin-dependent process has been shown to be responsible for the excessive protein degradation that occurs in conditions or disease states in which there is severe loss of body mass and negative nitrogen balance. A method of inhibiting the accelerated or enhanced proteolysis, a method of identifying inhibitors of the process, multipain and proteasome inhibitors are also disclosed.

Goldberg et al., in U.S. patent application Ser. No. 08/016, 066, filed Feb. 10, 1993, now abandoned disclose methods and drugs that inhibit the processing of antigens for presentation by major histocompatibility complex class I molecules. Specifically, inhibitors of the ATP-ubiquitin-dependent proteolytic pathway are described, which can inhibit MHC-I antigen presentation. These methods and drugs may be useful for the treatment of autoimmune diseases and for reducing rejection of organs and graft transplants. See, also, Michalek et al., *Nature* 363:552–554 (1993).

Tsubuki et al., *Biochem. and Biophys. Res. Commun.* 196(3):1195–1201 (1993) reported that a tripeptide aldehyde protease inhibitor, benzyloxycarbonyl(Z)-Leu-Leu-leucinal, initiates neurite outgrowth in PC12 cells at an optimal concentration of 30 nM. The following synthetic peptides are also mentioned: Z-Leu-Leu-Gly-H, Z-Leu-Leu-Ala-H, Z-Leu-Leu-Ile-H, Z-Leu-Leu-Val-H, Z-Leu-Leu-Nva-H, Z-Leu-Leu-Phe-H, Z-Leu-Leu-Leu-H, Bz-Leu-Leu-Leu-H, Ac-Leu-Leu-Leu-H, Z-Leu-Leu-Leu.sc, Z-Leu-Leu-Leu.ol, Z-Leu-Leu-Leu, Dns-Leu-Leu-Leu-H, Dns-Leu-Leu-Leu-CH$_2$Cl, and Leupeptin.

Siman et al. (WO 91/13904) disclose chymotrypsin-like proteases and their inhibitors. The inhibitors have the formula R-A4-A3-A2-Y, wherein R is hydrogen, or a N-terminal blocking group;

A4 is a covalent bond, an amino acid or a peptide;

A3 is a covalent bond, a D-amino acid, Phe, Tyr, Val, or a conservative amino acid substituent of Val;

A2 is a hydrophobic amino acid or lysine or a conservative amino acid substituent thereof, or when A4 includes at least two amino acids, A2 is any amino acid; and Y is a group reactive with the active site of said protease.

Powers (WO 92/12140) discloses peptide ketoamides, ketoacids, and ketoesters and their use in inhibiting serine proteases and cysteine proteases.

Bartus et al. (WO 92/1850) disclose uses for Calpain inhibitor compounds and pharmaceutical compositions containing them. One use of these compounds is in the treatment of a neurodegenerative pathology in a human patient. The disclosure also provides additional uses and pharmaceutical compositions containing Calpain inhibitor compounds, such as peptide ketoamides, peptide ketoacids, and peptide ketoesters.

SUMMARY OF THE INVENTION

The present invention relates to a method for reducing the cellular content and activity of NF-κB.

In a preferred embodiment, the present invention relates to a method for reducing the cellular content and activity of NF-κB in an animal comprising contacting cells of the animal with inhibitors of proteasome function or ubiquitin conjugation.

More particularly, the present invention is directed to a method for reducing the cellular content and activity of NF-κB in an animal comprising contacting cells of the animal with a proteasome function or ubiquitin conjugation inhibitor of the structure (1):

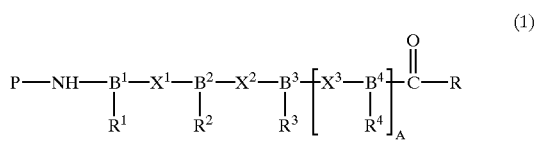

where
P is an amino-group-protecting moiety;
B$^1$, B$^2$, B$^3$, and B$^4$ are independently selected from the group consisting of

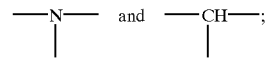

X$^1$, X$^2$, and X$^3$ are independently selected from the group consisting of

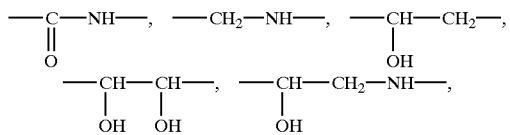

and —CH=CH—;
R is a hydrogen, alkyl, acyl, or carboxyl;
R$^1$, R$^2$, R$^3$, and R$^4$ are independently selected from the group consisting of hydrogen, alkyl, cycloalkyl, alkenyl, alkynyl, aryl, and —CH$_2$—R$^5$,
where R$^5$ is aryl, aralkyl, alkaryl, cycloalkyl or —Y—R$^6$, where Y is a chalcogen, and R$^6$ is alkyl; and
A is 0 or 1.

The "animals" referred to herein are preferably mammals. Both terms are intended to include humans.

BRIEF DESCRIPTION OF THE DRAWINGS

FIG. 3 depicts processing of p105/p60Tth in proteasome-depleted and proteasome-enriched extracts.

DESCRIPTION OF THE PREFERRED EMBODIMENTS

Figure 1:
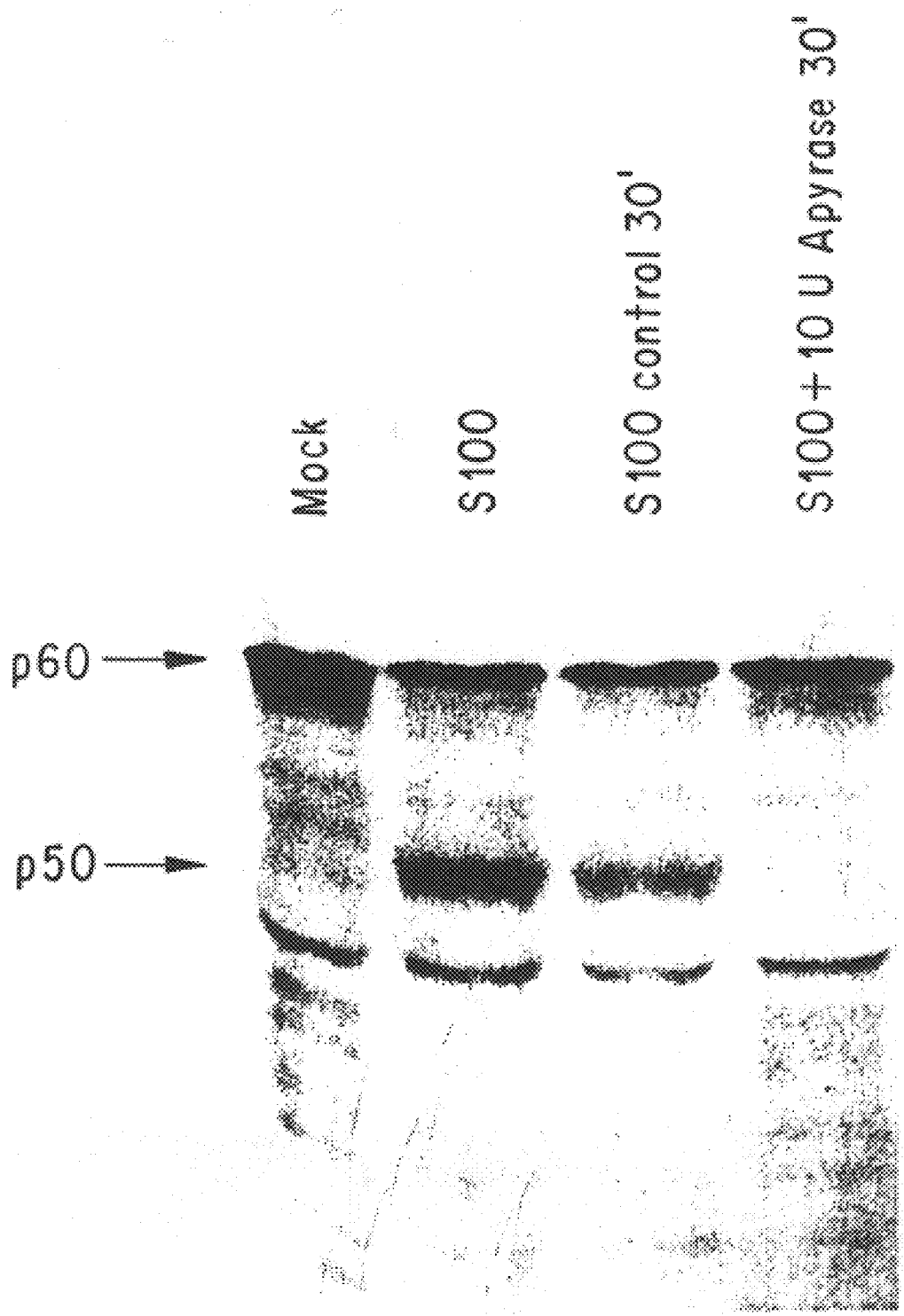
FIG. 1 shows that proteolytic processing of the p60Tth precursor to p50 in vitro requires ATP.
Figure 2:
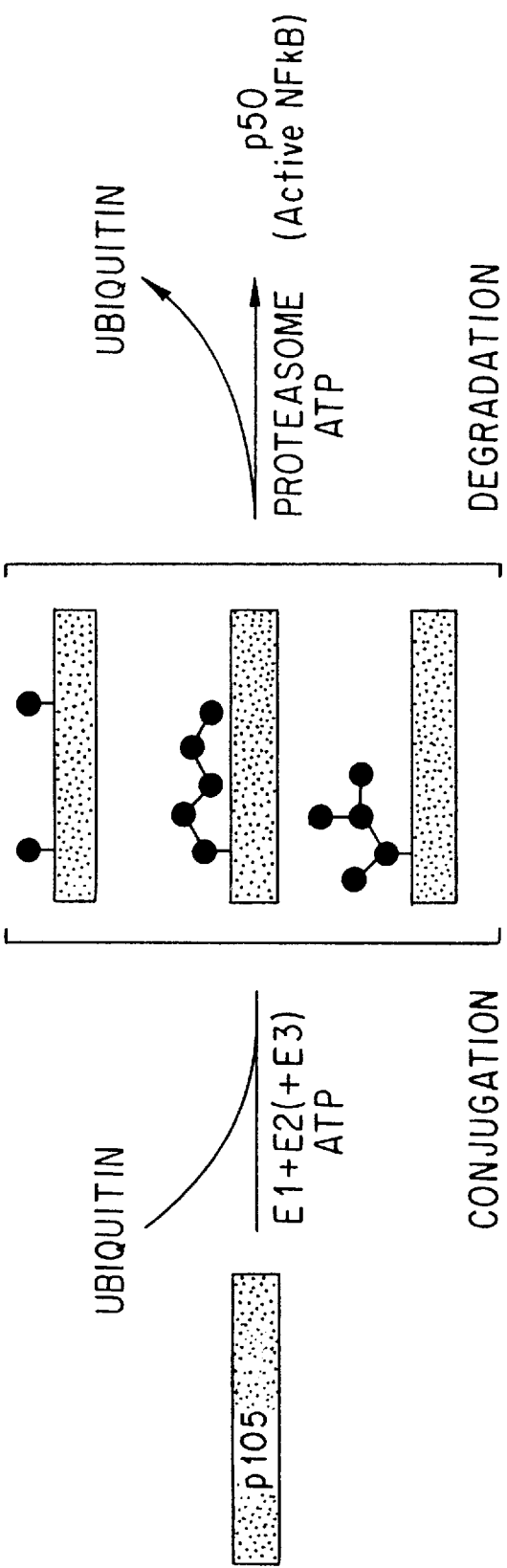
FIG. 2 is a diagram showing the role of ubiquitin and proteasome in the generation of active NF-κB.

NF-κB exists in an inactive form in the cytosol complexed with an inhibitor protein, IκB. In order for the NF-κB to become active and perform its function, it must enter the cell nucleus. It cannot do this, however, until the IκB portion of the complex is removed, a process referred to by those skilled in the art as the activation of, or processing of, NF-κB. In some diseases, the normal performance of its function by the NF-κB can be detrimental to the health of the patient. For example, as mentioned above, NF-κB is essential for the expression of the human immunodeficiency virus (HIV). Accordingly, a process that would prevent the activation of the NF-κB in patients suffering from such diseases could be therapeutically beneficial. The inhibitors employed in the practice of the present invention are capable of preventing this activation. Thus, blocking NF-κB activity or production could have important application in various areas of medicine, e.g., inflammation, sepsis, AIDS, and the like.

More specifically, the activity of NF-κB is highly regulated (Grilli et al., *International Review of Cytology* 143: 1–62 (1993); Beg et al., *Genes and Development* 7:2064–2070 (1993)). NF-κB comprises two subunits, p50 and an additional member of the rel gene family, e.g., p65 (also known as Rel A). In most cells, the p50 and p65 are present in an inactive precursor form in the cytoplasm, bound to IκB. In addition, the p50 subunit of NF-κB is generated by the proteolytic processing of a 105 kD precursor protein NF-κB$_1$ (p105), and this processing is also regulated. The sequence of the N-terminal 50 kD portion of p105 is similar to that of p65 and other members of the rel gene family (the rel homology domain). By contrast, the C-terminal 55 kD of p105 bears a striking resemblance to IκB-α (also known as MAD3). Significantly, unprocessed p105 can associate with p65 and other members of the rel family to form a p65/p105 heterodimer. Processing of p105 results in the production of p50, which can form the transcriptionally active P50/p65 heterodimer. The C-terminal IκB-α-homologous sequence of p105 is rapidly degraded upon processing.

There is another rel-related protein, NF-κB$_2$ (p100), that is similar to p105 in that it, too, is processed to a DNA binding subunit, p52 (Neri et al., *Cell* 67:1075 (1991); Schmid et al., *Nature* 352:733 (1991); Bours et al., *Molecular and Cellular Biology* 12:685 (1992); Mercurio et al., *DNA Cell Biology* 11:523 (1992)). Many of the structural and regulatory features of p100 are similar to p105. In addition, the p100 protein can also form a heterodimer with p65 and other rel family members.

In summary, the transcriptional activity of heterodimers consisting of p50 and one of the many rel family proteins, such as p65, can be regulated by at least two mechanisms. First, the heterodimers associate with IκB-α to form an inactive ternary cytoplasmic complex. Second, the rel family members associate with p105 and p100 to form inactive complexes. The ternary complex can be activated by the dissociation and destruction of IκB-α, while the p65/p105 and p65/p100 heterodimer can be activated by processing p105 and p100, respectively.

The dissociation of IκB-α can be induced by a remarkably large number of extracellular signals, such as lipopolysaccharides, phorbol esters, TNF-α, and a variety of cytokines. The IκB-α is then rapidly degraded. Recent studies suggest that p105 and p100 processing can also be induced by at least some of these extracellular signals. Neither the signal transduction pathways leading to NF-κB activation, nor the mechanisms of IκB-α inactivation or p105/p100 processing are understood. Accordingly, the inventors do not wish to be limited by any theory of the mechanism(s) by which the inhibitors employed in the practice of the present invention achieve their useful effects.

The inventors do have clear evidence of effects with certain inhibitors that block the hydrophobic site on the 20S (core) proteasome particle, but it must be realized that other essential sites exist on this particle, which constitutes the catalytic core on the 26S proteasome complex. Consequently, similar effects would be anticipated with inhibitors of other essential activities of the proteasome. Removal of the proteasome particle by ultracentrifugation or immunoprecipitation prevents the activation of NF-κB. There are many other catalytic functions on this particle that, if blocked, would also be expected by those skilled in the art to prevent its ability to process NF-κB and/or destroy IκB. It is also possible that the effects achieved by the inhibitors used in the process of the present invention may be achieved by inhibition of the ubiquitination of NF-κB and/or IκB. Indeed, the inventors have discovered that ubiquitin-conjugation is necessary for their degradation. Accordingly, there may be specific E-2s or E-3s involved in the processing of NF-κB and/or IκB whereby one could predict that any inhibitor of E-1, E-2, or E-3-dependent Ub-conjugation would prevent NF-κB activation by blocking the ubiquitin-proteasome pathway.

Studies have demonstrated that p105 or a truncated form of p105 (p60Tth) can be processed to p50 in vitro (Fan et al., *Nature* 354:395–398 (1991)). Certain of the requirements and characteristics of this in vitro processing reaction (e.g., ATP/Mg$^{++}$ dependency) suggested to the present inventors that the ATP-dependent protease complex of the ubiquitin-mediated protein degradation pathway was involved (i.e. proteasome; Rechsteiner, 1991, Goldberg, *Eur. J. Biochem.* 203:9–23 (1992), Hershko et al., *Annu. Rev. Biochem.* 61:761–807 (1992)). However, this structure was only known to catalyze the complete degradation of proteins to small acid-soluble peptides and was not believed capable of processing precursors to generate active proteins, such as p50 NF-κB.

Using a variety of experimental approaches, the present inventors have proven that the proteasome is indeed required for the processing of p105 to p50. First, it was found that the p105/p60Tth proteins are not processed in mammalian cell cytoplasmic extracts depleted of proteasome activity. However, addition of purified 26S proteasomes to these depleted extracts restores the processing activity. Second, specific inhibitors of the proteasome block the formation of p50 in mammalian cell extracts and in vivo. Third, mammalian p105 is processed to p50 in *Saccharomyces cerevisiae* in vivo, and a mutant in the chymotrypsin-like activity of the proteasome results in a significant decrease in p105 processing. p60Tth is ubiquitinated in vitro and this ubiquitination is a pre-requisite for p105 processing.

As mentioned above, the C-terminal half of the p105 (p105C') is rapidly degraded during the formation of p50 and the sequence of p105C' is remarkably similar to that of IκB. Because of the similarity in the structures and activities of p105C' and IκB-α, the present inventors initiated studies to determine whether the proteasome is also involved in the inactivation Of IκB-α. IκB-α is rapidly degraded in response to NF-κB inducers and this degradation has been shown to be necessary for the activation (Mellits et al., *Nucleic Acids Research* 21(22):5059–5066 (1993); Henkel et al., *Nature* 365:182–185 (1993); Beg et al., *Molecular and Cellular Biology* 13(6):3301–3310 (1993)). The present inventors have now shown that IκB-α degradation and the activation of NF-κB is indeed blocked by inhibitors of proteasome function or ubiquitin conjugation.

Accordingly, the proteasome plays an essential role in the regulation of NF-κB activity. First, the proteasome is required for the processing of p105 and possibly p100. The degradation of the inhibitory C-terminus may also require the proteasome. Second, the proteasome appears to be required for the degradation of IκB-α in response to extracellular inducers.

The present invention preferably relates to the use of inhibitors of proteasome function or ubiquitin conjugation of the structure (1):

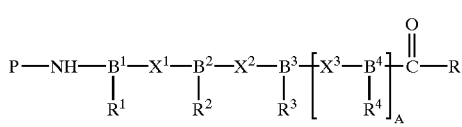

(1)

where

P is an amino-group-protecting moiety;

$B^1$, $B^2$, $B^3$, and $B^4$ are independently selected from the group consisting of

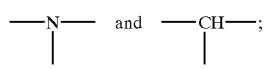

$X^1$, $X^2$, and $X^3$ are independently selected from the group consisting of

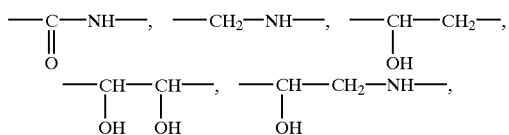

and —CH=CH—;

R is a hydrogen, alkyl, acyl, or carboxyl;

$R^1$, $R^2$, $R^3$, and $R^4$ are independently selected from the group consisting of hydrogen, alkyl, cycloalkyl, alkenyl, alkynyl, aryl, and —$CH_2$—$R^5$, where $R^5$ is aryl, aralkyl, alkaryl, cycloalkyl or —Y—$R^6$, where Y is a chalcogen, and $R^6$ is alkyl; and A is 0 or 1.

In a preferred embodiment of the present invention, the P moiety of the proteasome inhibitor is (2)

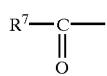

(2)

and $R^7$ is alkyl, aryl, alkaryl, aralkyl, alkoxy, aryloxy, alkaryloxy, or aralkoxy.

Where $R^7$ is alkyl, it is preferably alkyl of from 1 to 4 carbon atoms, e.g., methyl, ethyl, propyl, butyl, or isomers thereof. Additionally, where $R^7$ is alkaryl, aralkyl, alkoxy, alkaryloxy, or aralkoxy, the alkyl moiety thereof is also preferably one having from 1 to 4 carbon atoms.

Where $R^7$ is aryl, it is preferably aryl of from 6 to 10 carbon atoms, e.g., phenyl or naphthyl, which may, if desired, be ring substituted. Additionally, where $R^7$ is alkaryl, aralkyl, aryloxy, alkaryloxy, or aralkoxy, the aryl moiety thereof is also preferably one having from 6 to 10 carbon atoms.

It is more preferred that $R^7$ be alkyl or aralkoxy, most preferably methyl or benzyloxy, i.e.,

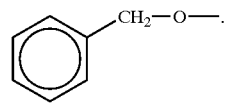

In structure (1), X represents a peptide bond or an isostere that can be used as a peptide bond replacement in the proteasome inhibitors to increase bioavailability and reduce hydrolytic metabolism. As noted above, X can be

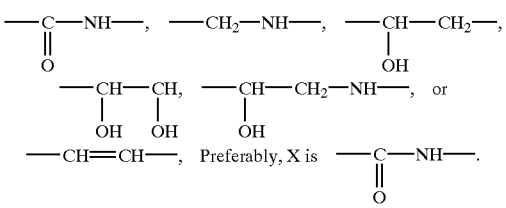

Introduction of these moieties into the proteasome inhibitors results in the following:

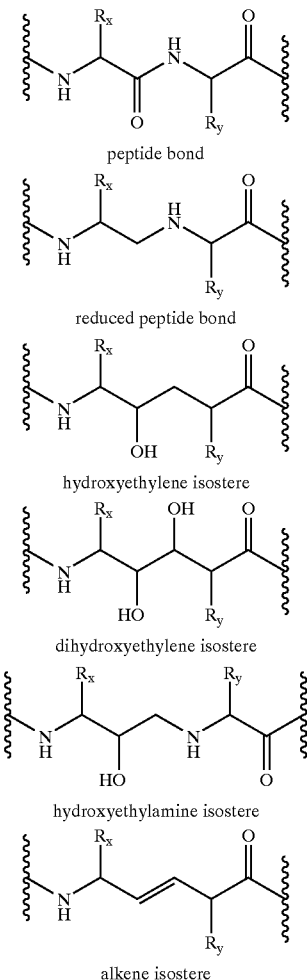

peptide bond reduced peptide bond hydroxyethylene isostere dihydroxyethylene isostere hydroxyethylamine isostere alkene isostere For example, if Z-Leu-Leu-Leu-H is found to undergo rapid hydrolytic metabolism to produce Z-Leu-OH and $H_2$N-Leu-Leu-H, the hydroxyethylene isostere can be prepared to eliminate this reaction:

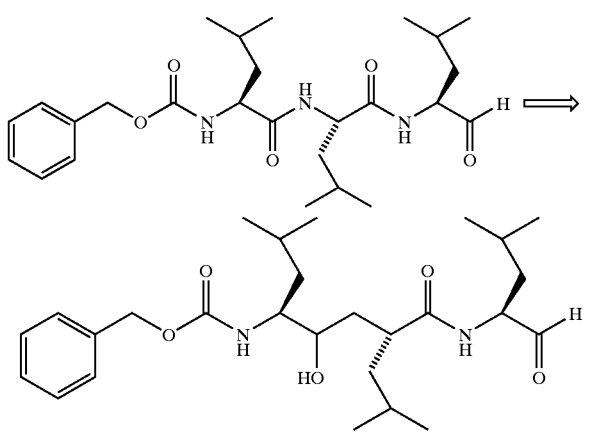

Another isostere within the scope of the present invention is the aza-peptide isostere. This is the result of the replacement of the α-carbon atom of an amino acid with a nitrogen atom, e.g.,

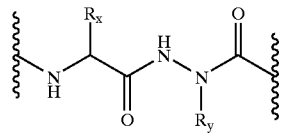

As noted above, A in structure (1) can be either 0 or 1. Thus, when A is 0, the amino acid residue within the brackets is not present and the inhibitor is a tripeptide. Similarly, where A is 1, the amino acid residue within the brackets is present and the inhibitor is a tetrapeptide. It is preferred that A be 0.

It is preferred that $R^1$ and $R^2$ in structure (1) be independently selected from the group consisting of alkyl and —$CH_2$—$R^5$. More preferably, $R^1$ and $R^2$ are independently selected from the group consisting of alkyl groups of from 1 to 4 carbon atoms, e.g., methyl, ethyl, propyl, butyl, or isomers thereof, e.g., isopropyl, isobutyl, sec-butyl, t-butyl, or —$CH_2$—$R^5$, where $R^5$ is cycloalkyl or naphthyl. It is more preferred that at least one of $R^1$ and $R^2$ be isobutyl,

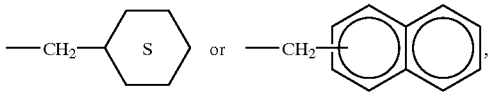

and most preferred that both $R^1$ and $R^2$ be isobutyl.

Where $R^3$ is alkyl, it is preferably alkyl of from 1 to 4 carbon atoms, e.g., methyl, ethyl, propyl, butyl, or isomers thereof, which groups may be substituted or unsubstituted.

Where $R^3$ is aryl, it is preferably aryl of from 6 to 10 carbon atoms, e.g., phenyl or naphthyl, which groups may be substituted or unsubstituted.

Where $R^3$ is a substituted alkyl, it is preferably an alkyl of from 1 to 4 carbon atoms substituted with at least one aryl group of from 6 to 10 carbon atoms or at least one cycloalkyl group, preferably a cycloalkyl group having 5 or 6 carbon atoms, which groups may be substituted or unsubstituted.

Where $R^3$ is substituted aryl, it is preferably substituted with at least one alkyl group of from 1 to 4 carbon atoms, which groups may be substituted or unsubstituted.

Where $R^3$ is cycloalkyl, it is preferably cycloalkyl of from 5 to 6 carbon atoms, e.g., cyclopentyl or cyclohexyl, which groups may be substituted or unsubstituted.

Where $R^3$ is substituted cycloalkyl, it is preferably substituted with at least one aryl group of from 6 to 10 carbon atoms or at least one alkyl group, preferably an alkyl group having 1 to 4 carbon atoms, which groups may be substituted or unsubstituted.

Where $R^3$ is —Y—$R^6$, Y is a chalcogen, preferably oxygen or sulfur, more preferably sulfur; and $R^6$ is alkyl, preferably alkyl of from 1 to 4 carbon atoms, e.g., methyl, ethyl, propyl, butyl, or isomers thereof.

R in the structure shown above is hydrogen, alkyl, acyl, or carboxyl.

Where R is alkyl, it is preferably alkyl of from 1 to 4 carbon atoms, e.g., methyl, ethyl, propyl, butyl, or isomers thereof.

Where R is acyl, it is preferably comprises a carbonyl moiety covalently bonded to an alkyl moiety of from 1 to 4 carbon atoms, e.g., methyl, ethyl, propyl, butyl, or isomers thereof, which may be substituted or unsubstituted.

Where R is carboxyl, it is preferably a carboxyl of the structure $[R^8]_n$—COO—, where $R^8$ is alkylene of from 1 to 4 carbon atoms, e.g., methylene, ethylene, propylene, butylene, and isomers thereof, and n is 0 or 1, and where the final O is normally bound to an alkyl group of 1 to 4 carbon atoms, which may be substituted or unsubstituted, thereby forming an ester.

R is preferably hydrogen, alkyl, or carboxyl; more preferably, hydrogen.

Examples of suitable proteasome inhibitors include, without limitation, the following compounds:

| | |
|---|---|
| Ac-Leu-Leu-Nle-H | (3) |
| Ac-Leu-Leu-Met-H | (4) |
| Z-Leu-Leu-Val-H | (5) |
| Z-Leu-Leu-Nle-H | (6) |
| Z-Leu-Leu-Phe-H | (7) |
| Z-Leu-Leu-Nal-H | (8) |
| Z-Leu-Leu-Gly-H | (9) |
| Z-Leu-Leu-Ala-H | (10) |
| Z-Leu-Leu-Abu-H | (11) |
| Z-Leu-Leu-Nva-H | (12) |

(13)

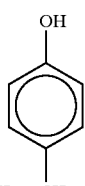

Z—Lue—Lue—NH—CH—CHO

| | |
|---|---|
| Z-Leu-Leu-Phe-C-O- | (14) |
| Z-Leu-Leu-Leu-H | (15) |
| Z-Leu-Leu-Ile-H | (16) |

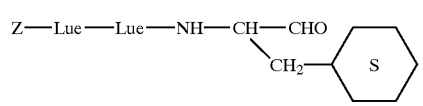 (17)
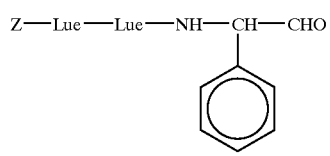 (18)
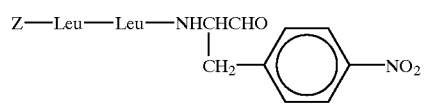 (20)
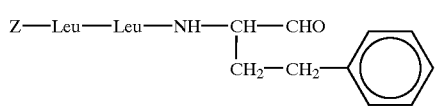 (21)
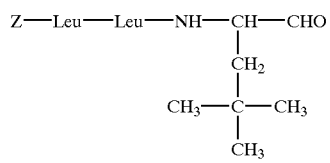 (22)
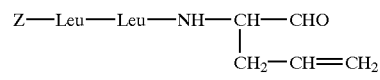 (23)
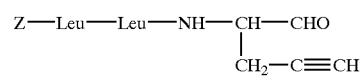 (24)
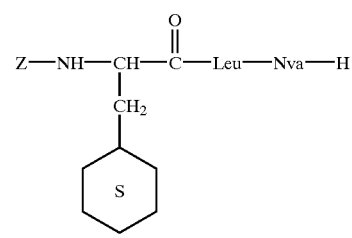 (25)
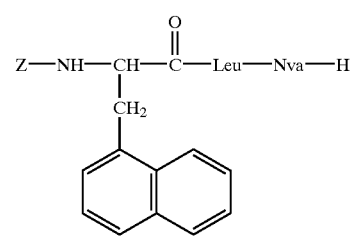 (26)
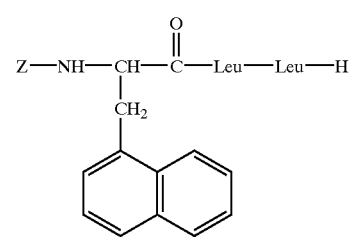 (27)
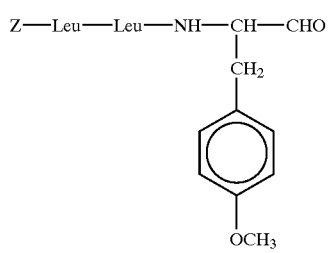 (28)
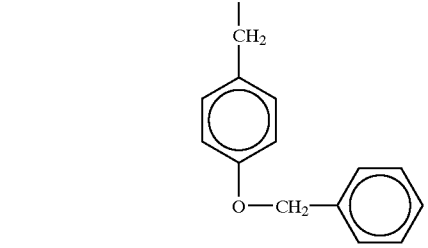 (29)
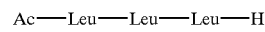 (30)
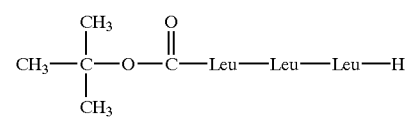 (31)
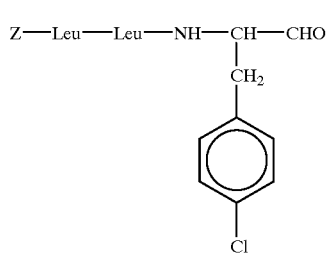 (32)
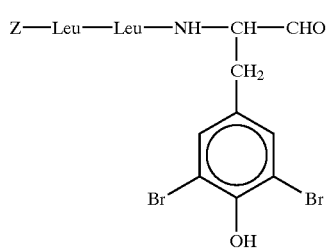 (33)
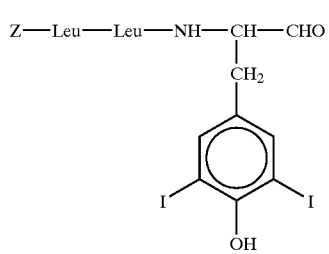 (34)

-continued
(35)
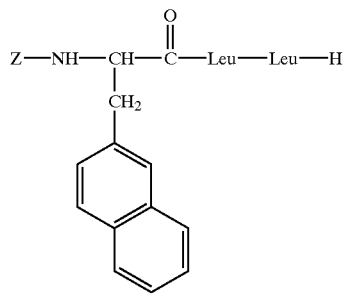
(36)
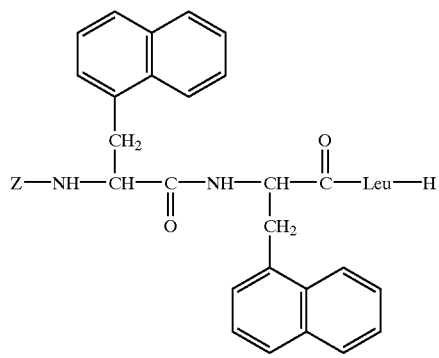
(37)
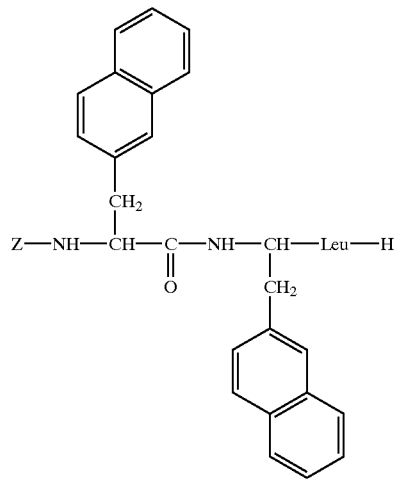
(38)
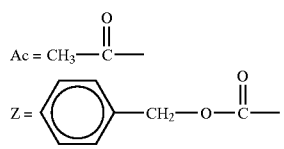
where:
Most preferably, the proteasome inhibitors are:
(39)
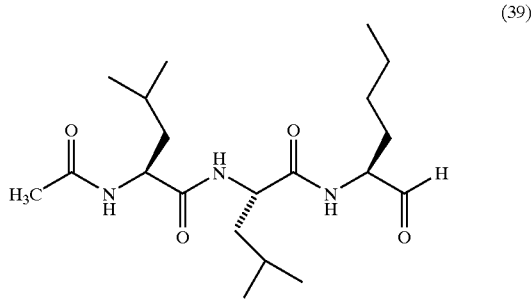
(40)
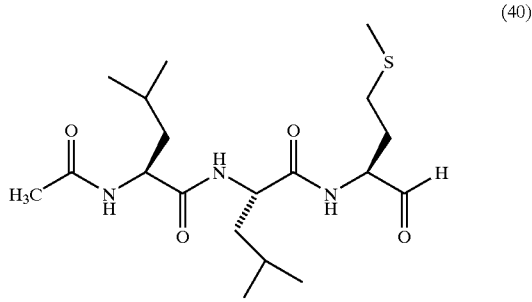
(41)
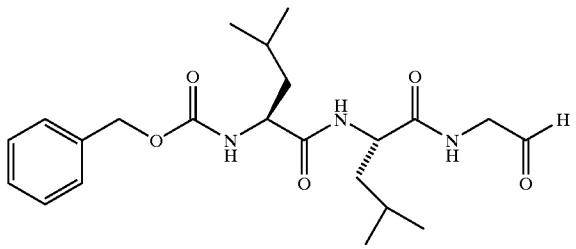
(42)
(43)
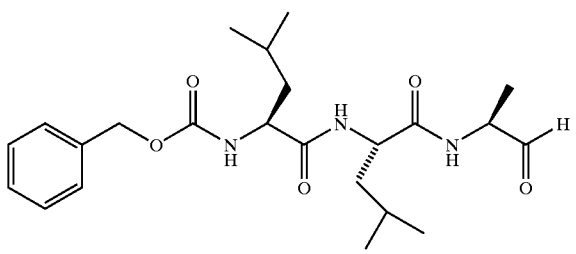

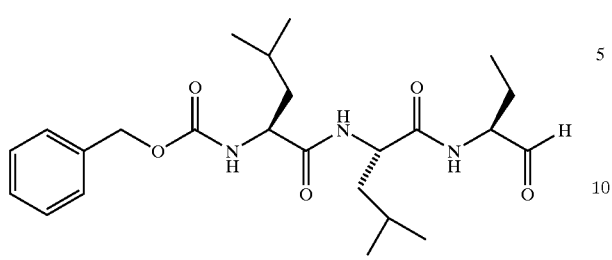
(44)
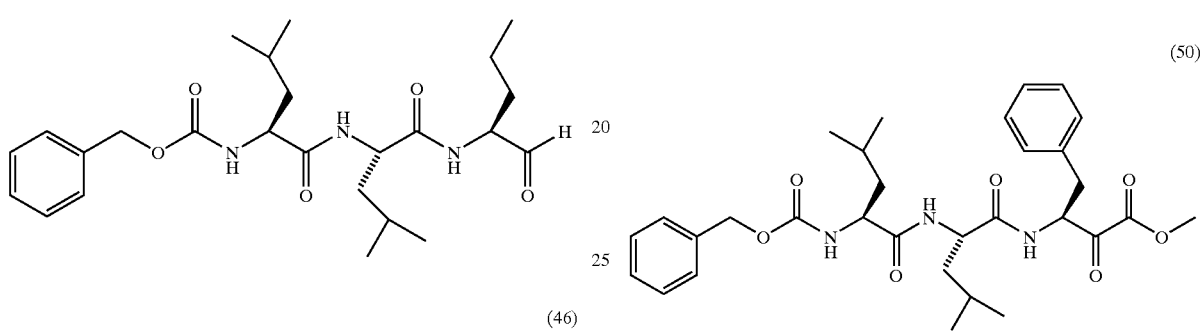
(45)
(46)
(47)
(48)
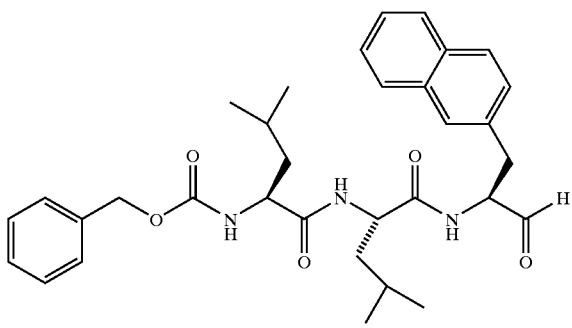
(49)
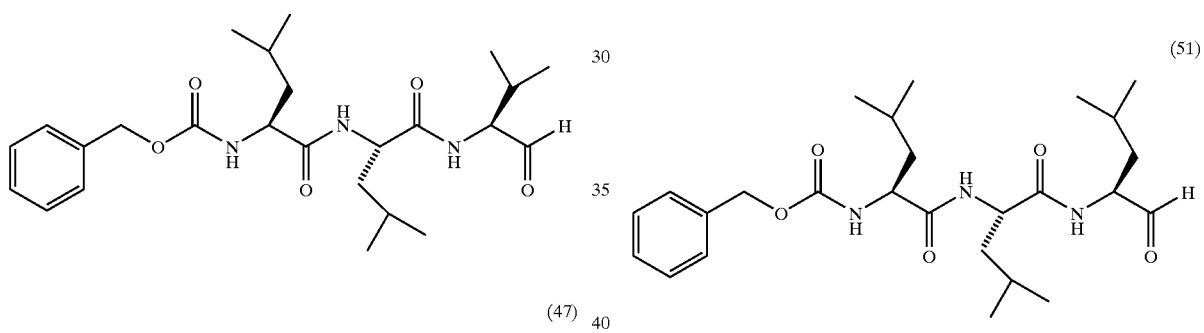
(50)
(51)
(52)
(53)

(54) 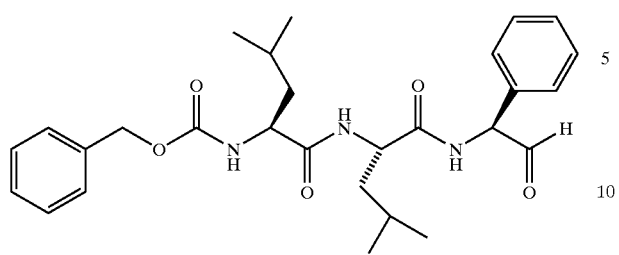
(55) 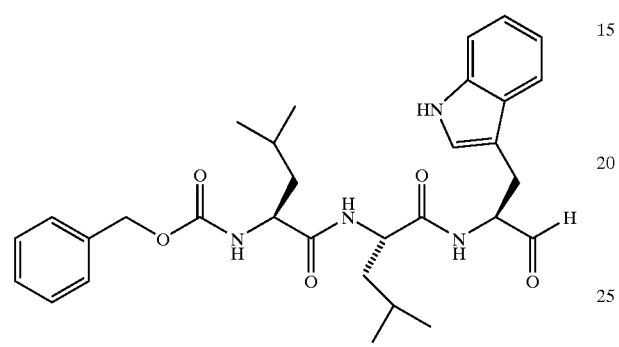
(56) 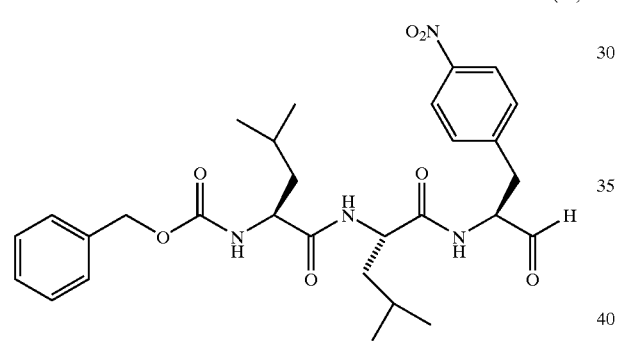
(57) 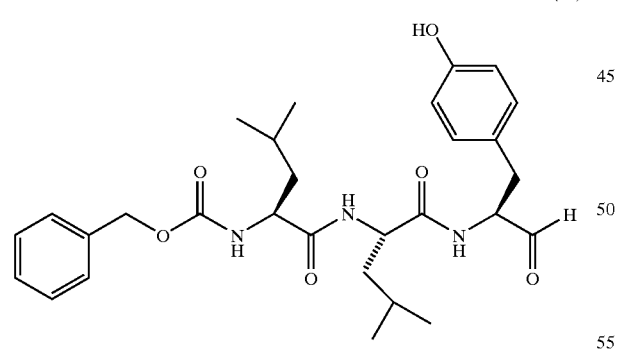
(58) 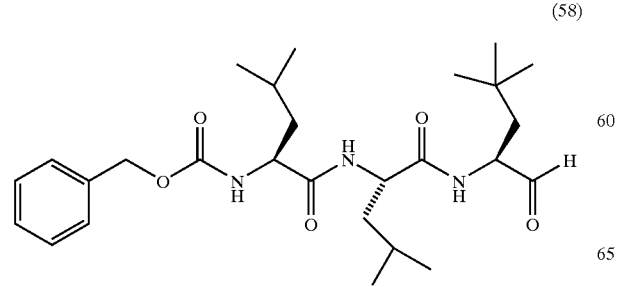
(59) 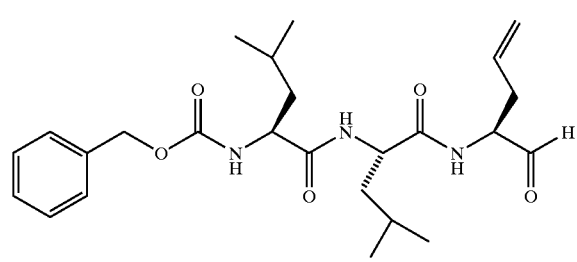
(60) 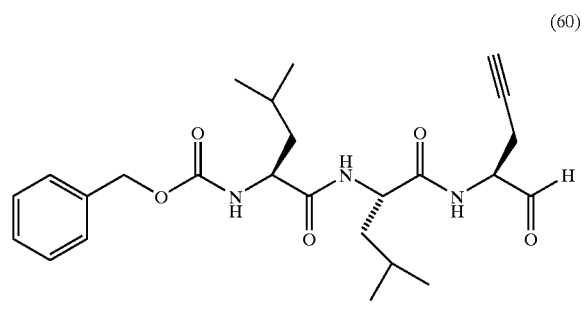
(61) 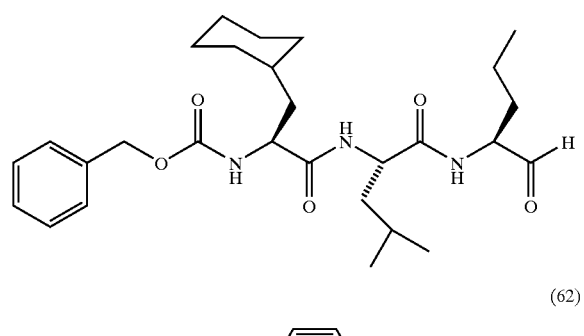
(62) 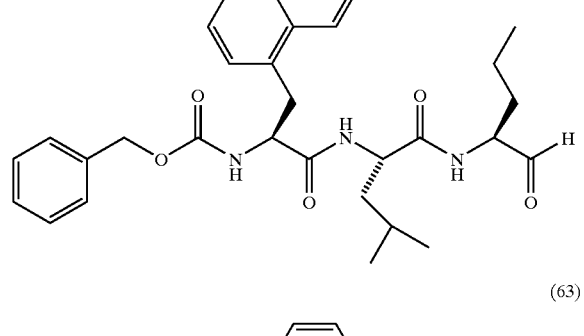
(63) 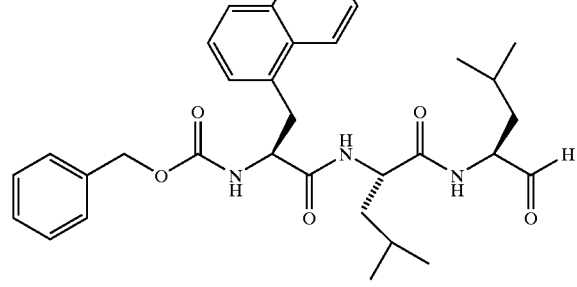

(64)
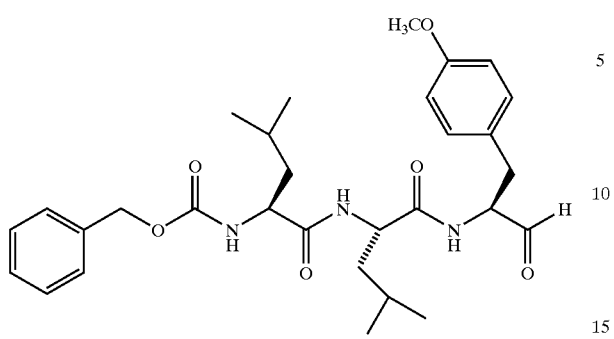
(65)
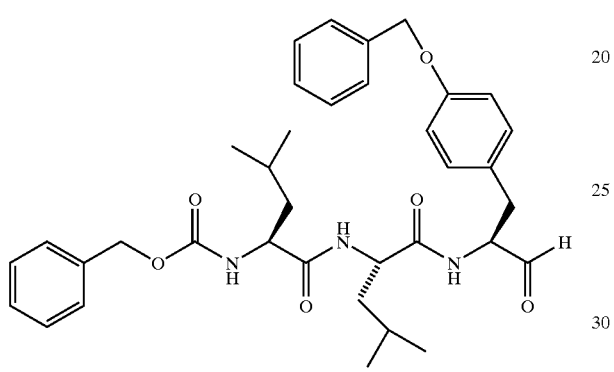
(66)
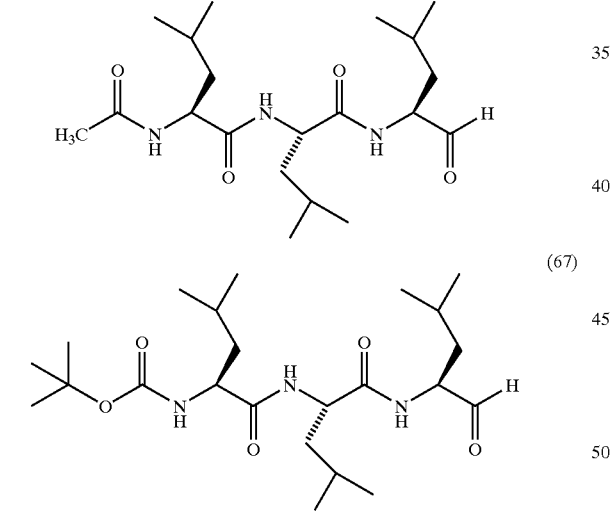
(67)
(68)
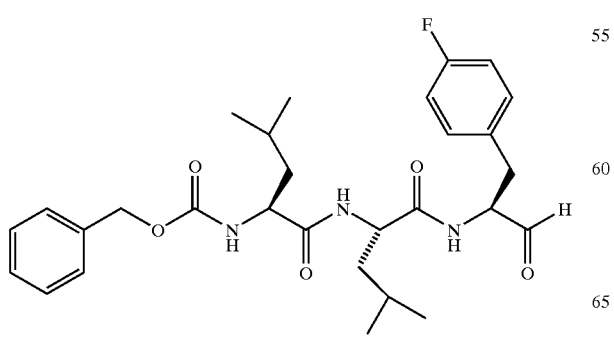
(69)
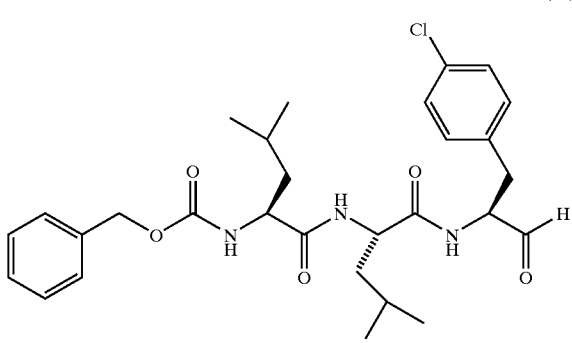
(70)
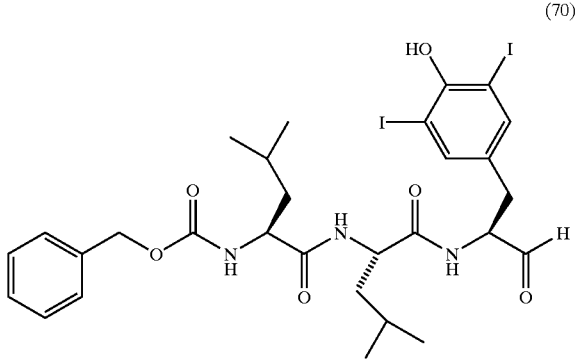
(71)
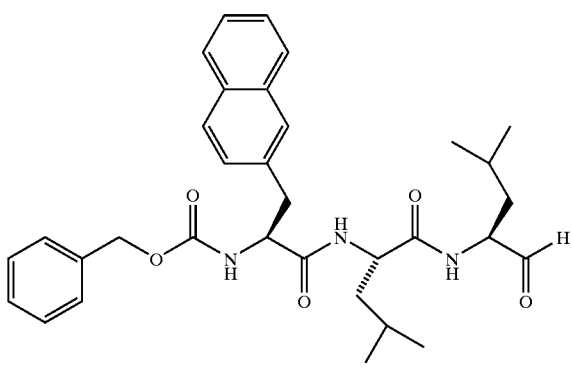
(72)
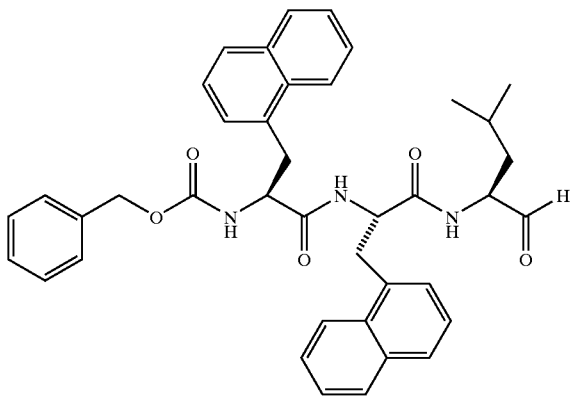

-continued

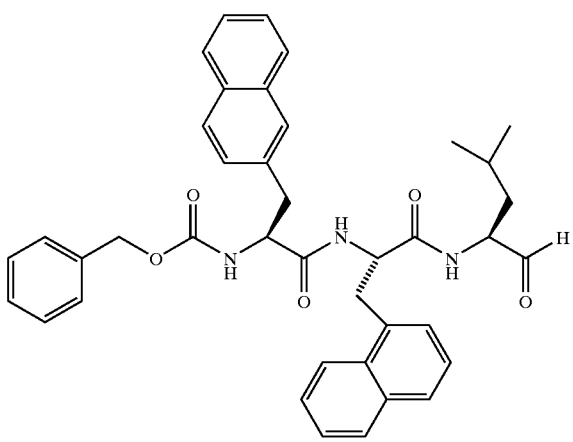

(73)

(74)

The present invention relates to a method for reducing the cellular content and activity of NF-κB in an animal comprising contacting cells of the animal with inhibitors of proteasome function or ubiquitin conjugation. In the present method, the accelerated proteolysis is inhibited by interfering with the ATP-Ub-dependent pathway at one or more possible steps (e.g., by interfering with activity of the 26S proteasome complex, or by interfering with activity of one of its components).

A particularly useful approach to testing drug candidates for their ability to inhibit the ATP-ubiquitin-dependent degradative process is to do so in cultured cells in which a short-lived protein whose degradation is ubiquitin-dependent is produced. Inhibition of the process leads to accumulation of the protein in the cytosol. The extent to which the protein accumulates in the cytosol can be determined, using known methods. For example, a potential inhibitor of the process can be introduced into cultured cells producing a short-lived enzyme and the extent to which the enzyme is present in the cytosol in the presence of the potential inhibitor can be compared with the extent to which it occurs in its absence. Accumulation of the enzyme in the presence of the potential inhibitor is indicative of inhibition of the ATP-ubiquitin-dependent processes by the potential inhibitor being tested. Cultured cells, such as COS cells, which are stably transformed with a gene encoding a short-lived protein whose degradation is ubiquitin-dependent (e.g., a short-lived enzyme, such as a mutant β-galactosidase from *E. coli*, whose half-life is about 15 minutes and whose degradation is ubiquitin-dependent) can be used (Bachmair, A. et al., *Science* 234:179–186 (1986); Gonda, D. K. et al., *J. Biol. Chem.* 264:16700–16712 (1989)). Other mutant forms of enzymes that are rapidly degraded can also be used. Accumulation of the mutant β-galactosidase in COS cytosol in the presence of a substance being assessed for its ability to inhibit the process (a potential inhibitor) is indicative of inhibition of the process. An appropriate control is COS cells maintained under the same conditions, but in the absence of the potential inhibitor. This approach can be used to screen for effective inhibitors from microbial broths or chemical libraries.

Tables I–III summarize results from kinetic experiments that measured the inhibition of the 20S and 26S proteasomes, as well as cathepsin B and calpain. In these tables, $K_i$ values are reported, which are dissociation constants for the equilibrium that is established when enzyme and inhibitor interact to form the enzyme:inhibitor complex.

The substances and assay conditions are briefly summarized in the footnotes to Table I. MG 101 and MG 102, also known as Calpain Inhibitor I and II, were purchased from Calbiochem as catalogue products.

TABLE I

PROTEASE SELECTIVITY OF N-ACETYL TRIPEPTIDE ALDEHYDES

| Inhibitor | | $K_i$ (nM) | | |
| --- | --- | --- | --- | --- |
| | 20 S[a] | 26 S[b] | Cat B[c] | Calpain[d] |
| MG 101 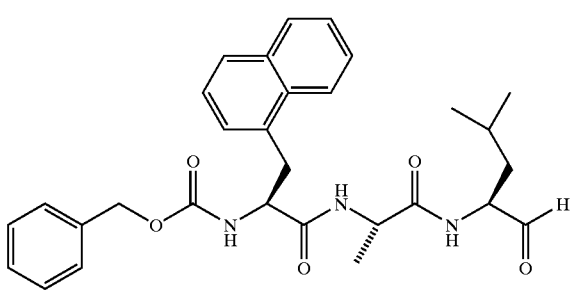 | 140* | 1,000 | 6 | 5 |

TABLE I-continued

PROTEASE SELECTIVITY OF N-ACETYL TRIPEPTIDE ALDEHYDES

| Inhibitor | $K_i$ (nM) | | | |
|---|---|---|---|---|
| | 20 S[a] | 26 S[b] | Cat B[c] | Calpain[d] |
| MG 102 | 1,000 | 28,000 | 94 | 120 |

[a] Rabbit muscle. SDS-activated. Suc-LLVY-AMC.
[b] Rabbit muscle. Substrate: Suc-Suc-LLVY-AMC-AMC. [Mg:ATP] = 2 mM.
[c] Bovine spleen. Substrate: Z-RR-AMC. [DTT] = 2 mM, [EDTA] = 5 mM, pH = 5.5, T = 37° C.
[d] Rabbit muscle, 80 kD catalytic subunit. Substrate: Suc-LLVY-AMC. [CaCl$_2$] = 1 mM, [DTT] = 2 mM, pH = 7.8, T = 20° C.

TABLE II

PROTEASE SELECTIVITY OF N-CARBOBENZOXY TRIPEPTIDE ALDEHYDES[a]

| Inhibitor | $K_i$ (nM) | | | |
|---|---|---|---|---|
| | 20 S | 26 S | Cat B | Calpain |
| MG 118 | 3,800 | 28,000 | 94 | 120 |
| MG 111 | 210 | 690 | 6 | 11 |
| MG 119 | 50 | 280 | 18 | 15 |

TABLE II-continued

PROTEASE SELECTIVITY OF N-CARBOBENZOXY TRIPEPTIDE ALDEHYDES[a]

| Inhibitor | $K_i$ (nM) | | | |
|---|---|---|---|---|
| | 20 S | 26 S | Cat B | Calpain |
| MG 115 | 21 | 78 | 10 | 10 |
| MG 120 | 94 | 560 | 36 | 14 |
| MG 114 | 47 | 120 | 7 | 12 |
| MG 110 | 48 | 180 | 100 | 62 |
| MG 121 | 25 | 70 | 73 | 62 |

[a]Same reaction conditions as listed in footnotes of Table I.

TABLE III

PROTEASE SELECTIVITY OF CARBOXY-ACTIVATED TRIPEPTIDES[a]

| Inhibitor | | $K_i$ (nM) | | | |
|---|---|---|---|---|---|
| | | 20 S | 26 S | Cat B | Calpain |
| MG 113 | 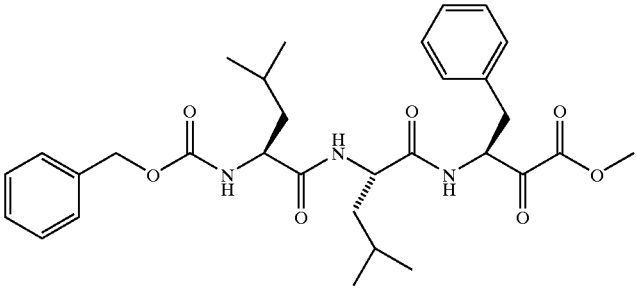 | 690 | 1,300 | <4 | 45 |

[a]Same reaction conditions as listed in footnotes of Table I.

Key Points to Note from Tables I–III:

(1) Peptide chain length is important for inhibitory potency against the 20S proteasome: compare the $K_i$ of 47 nM for Z-Leu-Leu-Nle-H (MG 114) with the $K_i$ of 15,000 nM for Z-Leu-Nle-H (MG 105; prepared by Calbiochem as catalogue product, not shown in tables).

(2) Potency against the 20S proteasome is also increased with increasing hydrophobicity of the N-terminal blocking group: compare the $K_i$ of 47 nM for Z-Leu-Leu-Nle-H (MG 114) with the $K_i$ of 140 nM for Ac-Leu-Leu-Nle-H (MG 101).

(3) In the series of compounds in Table II in which unbranched alkyl chain length is increased monotonically at the $P_1$ position (MG 118 (hydrogen), MG 111 (methyl), MG 119 (ethyl), MG 115 (n-propyl), and MG 114 (n-butyl)), there is a maximum of potency with Z-Leu-Leu-Nva-H (MG 115).

(4) Inhibitory potency against the 26S proteasome is always less than potency against the 20S proteasome. The difference is smallest for Z-Leu-Leu-Nva-H (MG 115; $K_{i,20S}$=21 nM and $K_{i,26S}$=78 nM), Z-Leu-Leu-Nal-H (MG 121; $K_{i,20}$S=25 nM and $K_{i,26S}$=70 nM), and Z-Leu-Leu-Phe-C(O)-OMe (Mg 113; $K_{i,20S}$=690 nM and $K_{i26S}$=1,300 nM).

(5) The peptide aldehydes that were examined more potently inhibit cathepsin B and calpain than they inhibit the 20S and 26S proteasome, except for the two inhibitors with large, hydrophobic $P_1$ residues, Z-Leu-Leu-Phe-H and Z-Leu-Leu-Nal-H (MG 110 and MG 121, respectively).

Data also show that MG 101 is an inhibitor of the 26S ATP-dependent protease and an inhibitor of the proteasome (macropain, multi-catalytic protease) (Table IV).

TABLE IV

MG 101 Inhibits Different Forms of Muscle Proteasome

| Enzyme Preparation | No Inhibitor Relative Catalytic Efficiency | MG 101 $K_i$ ($\mu$M) |
|---|---|---|
| 20S Proteasome | 1 | 7 |
| 26S Proteasome Complex | 2 | 3 |
| 20S Proteasome + Muscle 180 kDa Activator | 50 | 0.6 |
| 20S Proteasome + SDS | 140 | 0.14 |

The inhibitors can be used in vitro or in vivo. They can be administered by any number of known routes, including orally, intravenously, intramuscularly, topically, and by infusion (Platt et al., U.S. Pat. No. 4,510,130; Badalamente et al., *Proc. Natl. Acad. Sci. U.S.A.* 86:5983–5987 (1989); Staubli et al., *Brain Research* 444:153–158 (1988)) and will generally be administered in combination with a physiologically acceptable carrier (e.g., physiological saline). The effective quantity of inhibitor to be given will be determined empirically and will be based on such considerations as the particular inhibitor used, the condition of the individual, and the size and weight of the individual. They can be administered alone or in combination with another inhibitor or an inhibitor of another pathway.

Table V summarizes data for the inhibition of the 20S proteasome by various tripeptide aldehyde inhibitors.

TABLE V

Protease Selectivity of Miscellaneous Tripeptide Aldehydes

| Compound | $K_i$ (nM) |
|---|---|
| MG 124 | 59 |
| MG 129 | 60 |
| MG 131 | 6 |
| MG 132 | 9 |
| MG 133 | 470 |

TABLE V-continued

Protease Selectivity of Miscellaneous Tripeptide Aldehydes

| Compound | $K_i$ (nM) |
|---|---|
| MG 134 | 100 |
| MG 135 | 290 |
| MG 136 | 1,000 |
| MG 139 | 20 |
| MG 140 | 28 |

TABLE V-continued

Protease Selectivity of Miscellaneous Tripeptide Aldehydes

| Compound | | $K_i$ (nM) |
|---|---|---|
| MG 141 | [structure] | 50 |
| MG 142 | [structure] | 0.3 |
| MG 150 | [structure] | 0.4 |
| MG 151 | [structure] | 10 |

TABLE V-continued

Protease Selectivity of Miscellaneous Tripeptide Aldehydes

| Compound | $K_i$ (nM) |
|---|---|
| MG 152 | 6 |
| MG 153 | 280 |
| MG 154 | 75 |
| MG 155 | 54 |

TABLE V-continued

Protease Selectivity of Miscellaneous Tripeptide Aldehydes

| Compound | $K_i$ (nM) |
|---|---|
| MG 158 | 7 |
| MG 160 | 51 |
| MG 161 | 64 |
| MG 165 | 0.24 |

TABLE V-continued

Protease Selectivity of Miscellaneous Tripeptide Aldehydes

| Compound | | $K_i$ (nM) |
|---|---|---|
| MG 166 | | 0.035 |
| MG 167 | | 0.015 |
| MG 168 | | 0.49 |

The present invention will now be illustrated by the following examples, which are not intended to be limiting in any way.

EXAMPLES 1–3

Preparation of Peptidyl Aldehydes

All peptidyl N,O-dimethylhydroxylamides were prepared by solution phase method using 1-ethyl-3-(3-dimethylaminopropyl)carbodiimide hydrochloride as coupling reagent (Sheehan et al., *J. Am. Chem. Soc.* 87:2492–2493 (1965)). Reduction of the hydroxylamide with lithium aluminum hydride provided peptidyl aldehyde (Fehrentz et al., *Synthesis*: 676–678 (1983)); Fehrentz et al., *Int. J. Peptide Protein Res.* 26:236–241 (1985)); All compounds are characterized by Proton nuclei magnetic resonance (NMR) spectroscopy. The purity of the products was verified by thin layer chromatography and, in some cases, by high performance liquid chromatography (HPLC).

EXAMPLE 1

Preparation of Z-L-Leucine-L-leucine-L-norvalinal a) Boc-L-norvaline N,O-Dimethylhydroxylamide 1-Ethyl-3-(3-dimethylaminopropyl)carbodiimide hydrochloride (443 mg) in one portion was added to a mixture of N-Boc-L-norvaline dicyclohexylammonium salt (838 mg), N,O-dimethylhydroxylamine hydrochloride (215 mg), 1-hydroxybenzotriazole monohydrate (340 mg), and N-methylmorpholine (0.28 ml) in dimethyl formamide (DMF, 20 ml) at 0° C. The mixture was stirred at 0° C. for 2 hours, then at room temperature for 40 hours. The reaction was quenched with water (80 mL) and the mixture was extracted with ethyl acetate (EtOAc, 3×100 mL). The combined organic layers were washed with aqueous 10% hydrogen chloride (HCl), saturated sodium bicarbonate (NaHCO₃), and brine, then dried over anhydrous magnesium sulfate (MgSO₄), filtered, and evaporated to afford the product (546 mg) as an oil.

b) Z-L-Leucine-L-leucine-L-norvaline N,O-Dimethylhydroxylamide

A solution of N-Boc-L-norvaline N,O-dimethylhydroxylamide (546 mg) and trifluoroacetic acid (8 mL) in methylene chloride (20 mL) was stirred at 0° C. for 3 hours. The solvent was evaporated under reduced pressure and the residue was dried under vacuum. To this flask was added Z-L-leucine-L-leucine (794 mg), 1-hydroxybenzotriazole monohydrate (340 mg), N-methylmorpholine (0.28 mL), and DMF (20 mL). 1-Ethyl-3-(3-dimethylaminopropyl)carbodiimide hydrochloride (442 mg) was then added at 0° C. The mixture was stirred at 0° C. for 2 h, then at room temperature for 24 h. The reaction was quenched with water (40 mL) and the mixture was extracted with EtOAc (3×60 mL). The combined organic layers were washed with aqueous 10% HCl, saturated NaHCO₃, and brine, then dried over anhydrous MgSO₄, filtered, and evaporated to afford the product (1.09 g) as a white solid.

c) Z-L-Leucine-L-leucine-L-norvalinal

A solution of Z-L-leucine-L-leucine-L-norvaline N,O-dimethylhydroxylamide (1.09 g) was dissolved in 20 mL dry tetrahydrofuran (THF) and cooled to 0° C. Lithium aluminum hydride (1 M solution in THF, 3.05 mL) was added and the mixture was stirred at 0° C. for 25 minutes. Potassium bisulfate (465 mg) in 20 mL water was added and the mixture was extracted with EtOAc (3×80 mL). The combined organic layers were washed with aqueous 5% HCl, saturated NaHCO₃, and brine, then dried over anhydrous MgSO₄, filtered, and evaporated to afford the product (430 mg) as a white solid.

EXAMPLE 2

Preparation of Z-L-Leucine-L-leucine-L-leucinal a) Boc-L-Leucine-L-leucine N,O-Dimethylhydroxylamide A mixture of N-Boc-L-leucine-L-leucine (1 g), N,O-dimethylhydroxylamine hydrochloride (423 mg), 1-hydroxybenzotriazole monohydrate (509 mg), and N-methylmorpholine (0.42 mL) was dissolved in DMF (20 mL). 1-Ethyl-3-(3-dimethylaminopropyl)carbodiimide hydrochloride (610 mg) was added at 0° C. for 2 h, then at room temperature for 40 h. The reaction was quenched with water (80 mL) and the mixture was extracted with EtOAc (3×100 mL). The combined organic layers were washed with aqueous 10% HCl, saturated NaHCO₃, and brine then dried over anhydrous MgSO₄, filtered, and evaporated to afford the product (923 mg) as a white solid.

b) Z-L-Leucine-L-leucine-L-leucine N,O-Dimethylhydroxylamide

A solution of N-Boc-L-leucine-L-leucine N,O-dimethylhydroxylamide (923 mg) and trifluoroacetic acid (10 mL) in methylene chloride (20 mL) was stirred at 0° C. for 3 hours. The solvent was evaporated under reduced pressure and the residue was dried under vacuum. A portion of this product (488 mg) was transferred to another flask and was combined with Z-L-leucine (451 mg), 1-hydroxybenzotriazole monohydrate (276 mg), N-methylmorpholine (0.22 mL), and DMF (15 mL). 1-Ethyl-3-(3-dimethylaminopropyl) carbodiimide hydrochloride (357 mg) was then added at 0° C. The mixture was stirred at 0° C. for 2 h, then at room temperature for 42 h. The reaction was quenched with water (50 mL) and the mixture was extracted with EtOAc (3×60 mL). The combined organic layers were washed with aqueous 10% HCl, saturated NaHCO₃, and brine, then dried over anhydrous MgSO₄, filtered, and evaporated to afford the product as a white solid. This was further purified by silica gel chromatography (hexane/acetone 80:20, 70:30) to give the title compound (546 mg) as a white solid.

c) Z-L-Leucine-L-leucine-L-leucinal

A solution of Z-L-leucine-L-leucine-L-leucine N,O-dimethylhydroxylamide (546 mg) was dissolved in 15 mL dry tetrahydrofuran (THF) and cooled to 0° C. Lithium aluminum hydride (1 M solution in THF, 4.1 mL) was added and the mixture was stirred at 0° C. for 30 minutes. Potassium bisulfate (1.39 g) in 30 mL water was added and the mixture was extracted with EtOAc (3×50 mL). The combined organic layers were washed with aqueous 5% HCl, saturated NaHCO₃, and brine, then dried over anhydrous MgSO₄, filtered, and evaporated to afford the product (446 mg) as a white solid. This was further purified by reverse phase HPLC (water/acetonitrile).

EXAMPLE 3

Preparation of Z-L-(2-Naphthyl)-alanine-L-(1-naphthyl)-alanine-L-leucinal a) Boc-L-Leucine N,O-Dimethylhydroxylamide A mixture of N-Boc-L-leucine (2.47 g), N,O-dimethylhydroxylamine hydrochloride (1.09 g), 1-hydroxybenzotriazole monohydrate (1.51 g), and N-methylmorpholine (1.21 mL) was dissolved in DMF (40 mL), 1-Ethyl-3-(3-dimethylaminopropyl)carbodiimide hydrochloride (2.14 g) was added at 0° C. and the mixture was stirred at 0° C. for 2h, then at room temperature for 22 h. The reaction was quenched with water (100 mL) and the mixture was extracted with EtOAc (3×100 mL). The combined organic layers were washed with aqueous 10% HCl, saturated NaHCO₃, and brine, then dried over anhydrous MgSO₄, filtered, and evaporated to afford the product (2.57 g) as an oil.

b) Boc-L-(1-Naphthyl)-alanine-L-leucine N,O-Dimethylhydroxylamide

A solution of N-Boc-L-leucine N,O-dimethylhydroxylamide (983 mg) and trifluoroacetic acid (8 mL) in methylene chloride (20 mL) was stirred at 0° C. for 3 hours. The solvent was evaporated under reduced pressure and the residue was dried under vacuum. A portion of this product (208 mg) was transferred to another flask and was combined with Boc-L-(1-naphthyl)-alanine (378 mg) 1-hydroxybenzotriazole monohydrate (178 mg) N-methylmorpholine (0.15 mL), and DMF (10 mL). 1-Ethyl-3(3-dimethylaminopropyl) carbodiimide hydrochloride (241 mg) was then added at 0° C. The mixture was stirred at 0° C. for 2 h, then at room temperature for 17 hours. The reaction was quenched with water (20 mL) and the mixture was extracted with EtOAc (3×50 mL). The combined organic layers were washed with aqueous 10% HCl, saturated NaHCO₃, and brine, then dried over anhydrous MgSO₄, filtered, and evaporated to afford the product as a white solid (459 mg).

c) Z-L-(2-Naphthyl)-alanine-L-(1-naphthyl)-alanine-L-leucine-N,O-dimethylhydroxylamide A solution of Boc-L-(1-naphthyl)-alanine-L-leucine N,O-dimethylhydroxylamide (459 mg), trifluoroacetic acid (5 mL), and thioanisole (2 mL) was stirred at 0° C. for 2.5 hours. The solvent was evaporated and the residue was dried under vacuum. A portion of this product (182 mg) was transferred to another flask and was combined with Z-L-(2-naphthyl)-alanine (171 mg), 1-hydroxybenzotriazole monohydrate (99 mg), N-methylmorpholine (0.08 mL), and DMF (10 mL). 1-Ethyl-3-(3-dimethylaminopropyl) carbodiimide hydrochloride (112 mg) was then added at 0° C. The mixture was stirred at 0° C. for 2 h, then at room temperature for 41 hours. The reaction was quenched with water (20 mL) and the mixture was extracted with EtOAc (3×50 mL). The combined organic layers were washed with aqueous 10% HCl, saturated NaHCO$_3$, and brine, then dried over anhydrous MgSO$_4$, filtered, and evaporated to afford the product as a white solid. This was then purified by silica gel chromatography (hexane/acetone 80:20, 70:30) to give the title compound (321 mg).

d) Z-L-(2-Naphthyl)-alanine-L-(1-naphthyl)-alanine-L-leucinal

Z-L-(2-naphthyl)-alanine-L-(1-naphthyl)-alanine-L-leucine-N,O-dimethylhydroxylamide (321 mg) was dissolved in 15 mL dry tetrahydrofuran (THF) and cooled to 0° C. Lithium aluminum hydride (1 M, solution in THF, 1.7 mL) was added and the mixture was stirred at 0° C. for 30 minutes. Potassium bisulfate (0.59 g) in 30 mL water was added and the mixture was extracted with EtOAc (3×40 mL). The combined organic layers were washed with aqueous 5% HCl, saturated NaHCO$_3$, and brine, then dried over anhydrous MgSO$_4$, filtered, and evaporated to afford the product (274 mg) as a white solid.

EXAMPLE 4

Proteolytic Processing of the p60Tth Precursor to p50 in vitro Requires ATP

The p60Tth precursor (or p105) was translated in wheat germ extract. The substrate protein was mixed with HeLa cell cytoplasmic extract (S100) in a processing buffer containing 12 mM Tris, pH 7.5, 60 mM KCl, 20 mM creatine phosphate, 3.5 mM MgCl$_2$ and 1 mM ATP. After incubation at 30° C. for one hour, the reaction mixtures were subjected to immunoprecipitation with anti-p50 Ab and the proteins were resolved by SDS-PAGE. In the Apyrase treated sample, the p60 was incubated with 10 U of enzyme at 37° C. for 30 minutes to inactivate residual ATP in the wheat germ extract before adding the HeLa cell S100. The control sample did not receive the enzyme or ATP. The results are shown in FIG. 1.

EXAMPLE 5

Processing of p105/p60Tth in Proteasome-depleted and Proteasome-enriched Extracts HeLa cell S100 was centrifuged for six hours at 100,000×g to remove proteasomes. Loss of proteasome activity was verified using a fluorogenic peptide assay specific for the proteasome. The results from two different depleted extracts [Pr$^-$(I & II)] are shown. The pellet contains most of the proteasome activity. The processing reactions were carried out as described in Example 4 and the reactions were immunoprecipitated with either anti-p50 Ab or anti-myc peptide mAb. The anti-myc mAb will recognize the N-terminal myc-peptide on a tagged p60 precursor protein. The results are shown in FIG. 3.

EXAMPLE 6

Immunodepletion of the Proteasome Inhibits the Processing of NF-κB$_1$

Figure 4:
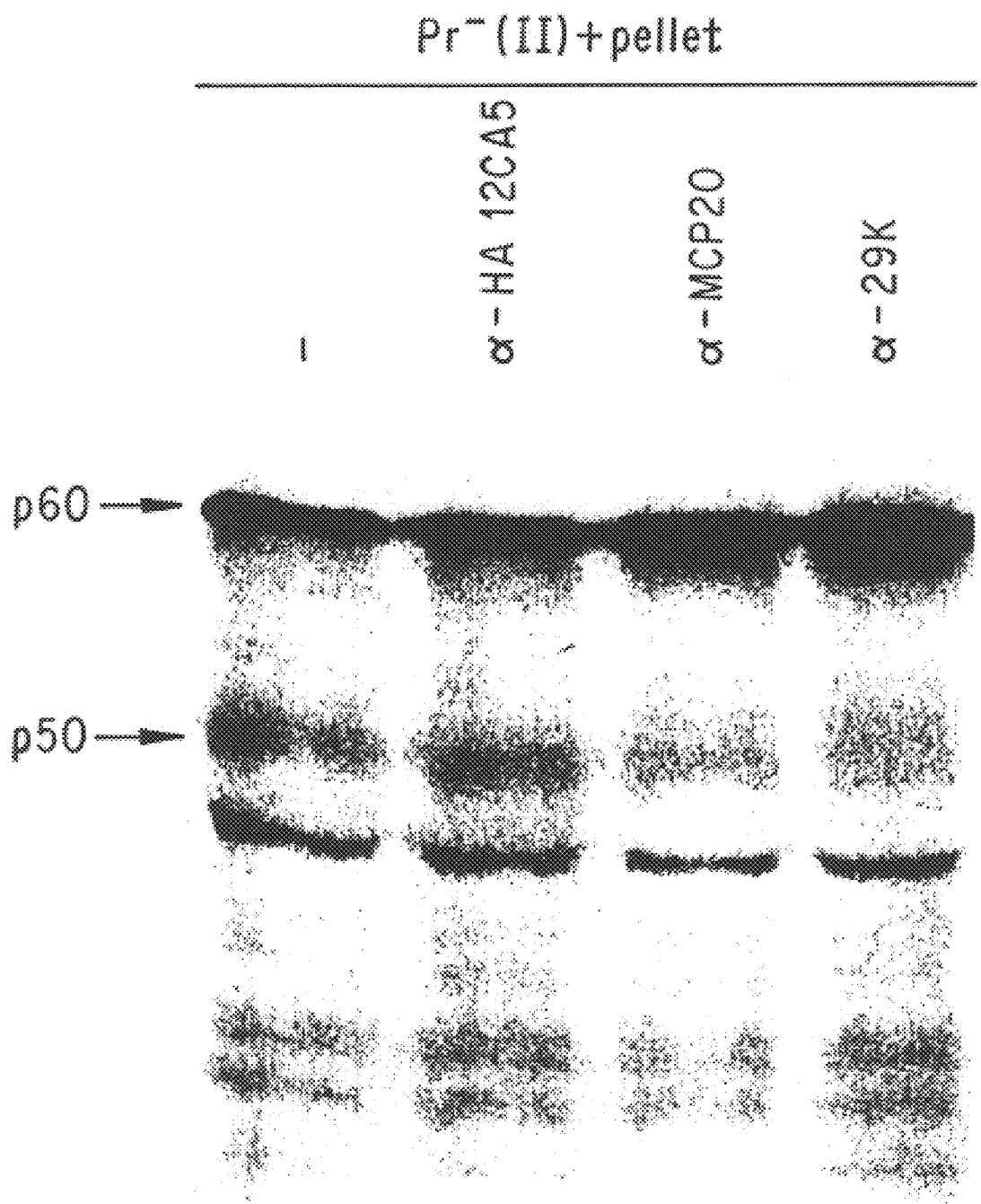
FIG. 4 shows that immunodepletion of the proteasome inhibits the processing of NF-κB.

Monoclonal antibodies against specific components of the proteasome (MCP20, 29K) and a control McAb against hemagglutinin (HA 12CA5) were incubated with Pr$^-$(II) extract reconstituted with proteasome activity from the pellet. The immune complexes were removed and the depleted extracts were used in p60 processing reactions as described in Example 4. The results are shown in FIG. 4.

EXAMPLE 7

Purified Proteasomes Stimulate the Processing of p60Tth

Figure 5A:
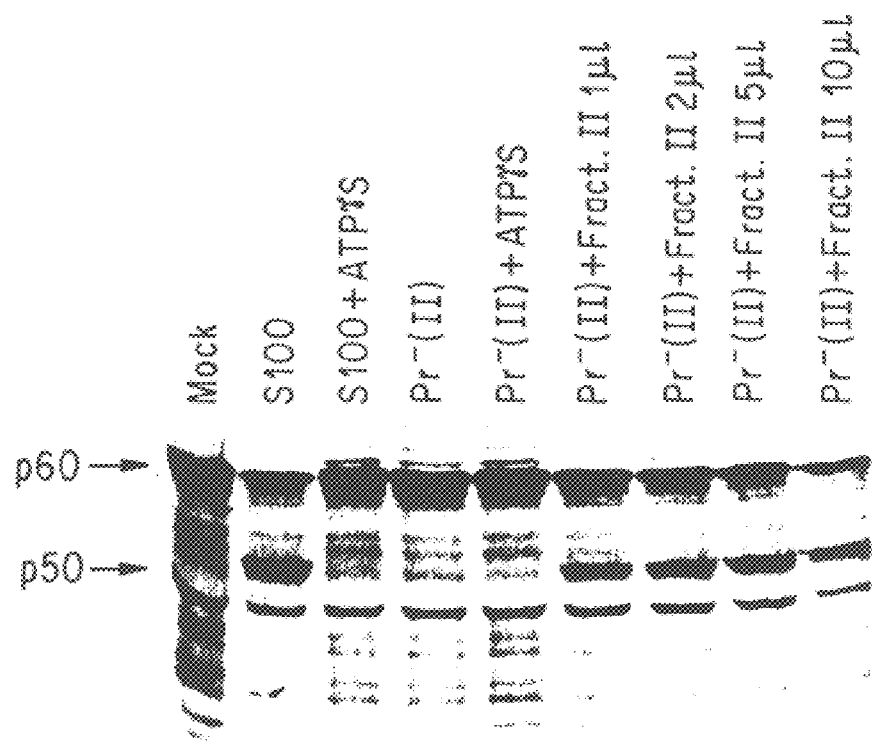
FIG. 5 shows that purified proteasomes stimulate the processing of p60Tth.
Figure 5B:
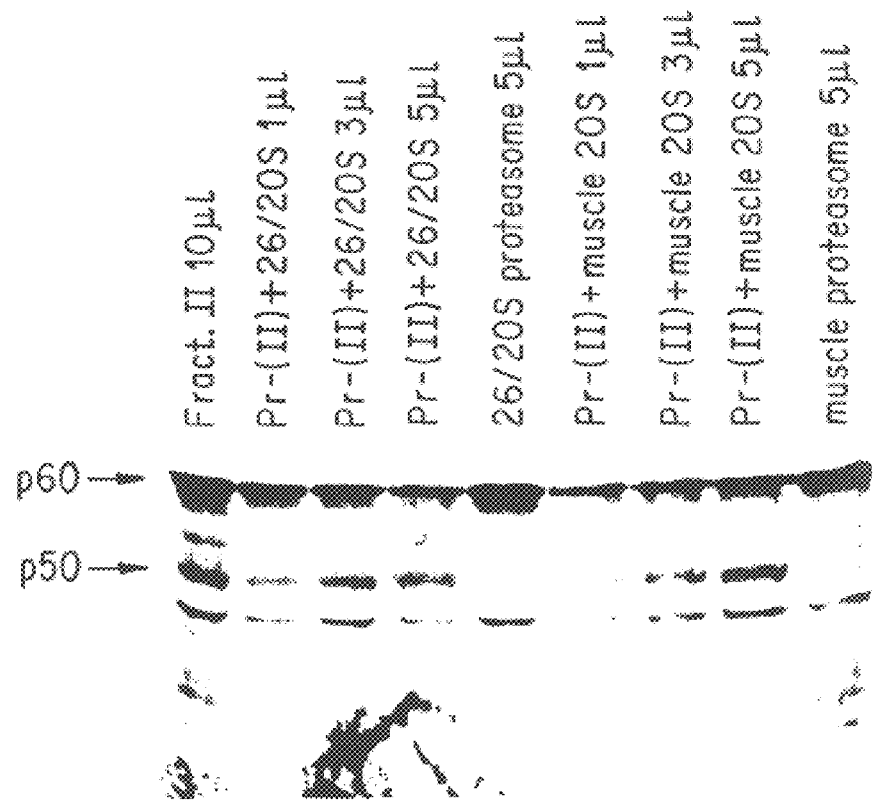

Increasing amounts of purified 20/26S proteasomes or a proteasome-enriched fraction from reticulocyte lysate, fraction II, were added alone or were combined with Pr$^-$(II) extract in a processing reaction (see Example 4). In addition, processing was inhibited by ATPγS, a non-hydrolyzable analogue of ATP that allows ubiquitination but inhibits proteasome function (lanes 3–5). See FIG. 5.

EXAMPLE 8

The p60Tth Precursor Protein is Ubiquitinated

Figure 6:
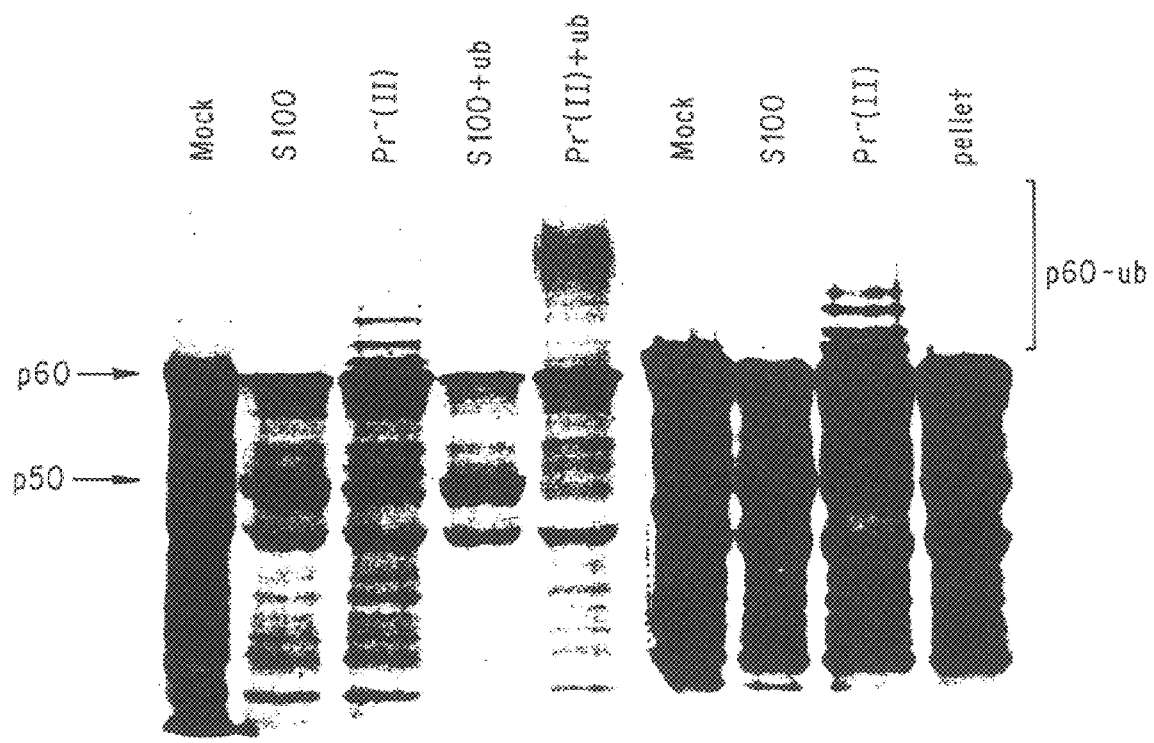
FIG. 6 shows that the p60Tth precursor protein is ubiquitinated.

In this Example, and in those described above, there are ladder-like bands that appear when the substrate is incubated with extracts lacking proteasome activity (Pr$^-$). The ubiquitination of p60 is more pronounced when 7.5 µg of purified ubiquitin (ub) is added to the Pr$^-$(II) extract in a processing reaction (lane 5). See FIG. 6.

EXAMPLE 9

Ubiquitin is Required for the Processing of NF-κB$_1$

A. Different amounts of reticulocyte fraction II (+/−7.5 µg of ub) were used in a processing reaction (see Example 4) with p60 as substrate. Fraction II has proteasome activity, but has very little ubiquitin.

B. HeLa cell S100 or fraction II was supplemented with E. coli recombinant wild-type ub or mutant ub(L>R48) protein, which inhibits ub chain formation. Processing reactions were as described above.

Figure 7A:
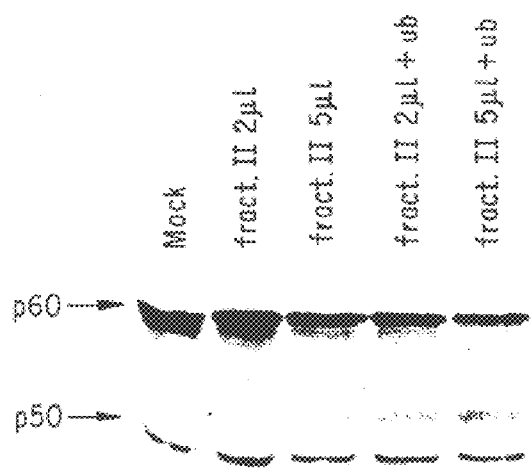
FIGS. 7A, 7B, and 7C show that ubiquitin is required for the processing of NF-κB.
Figure 7B:
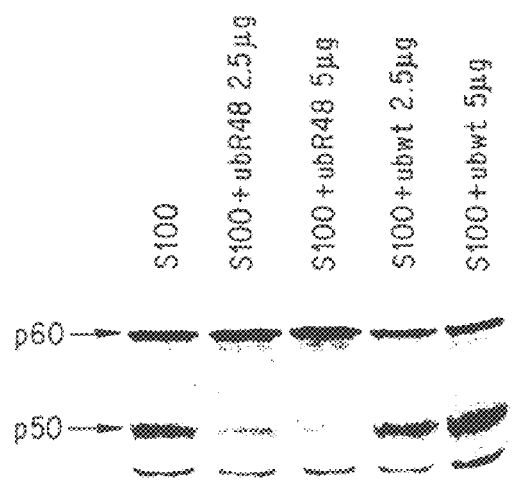
Figure 7C:
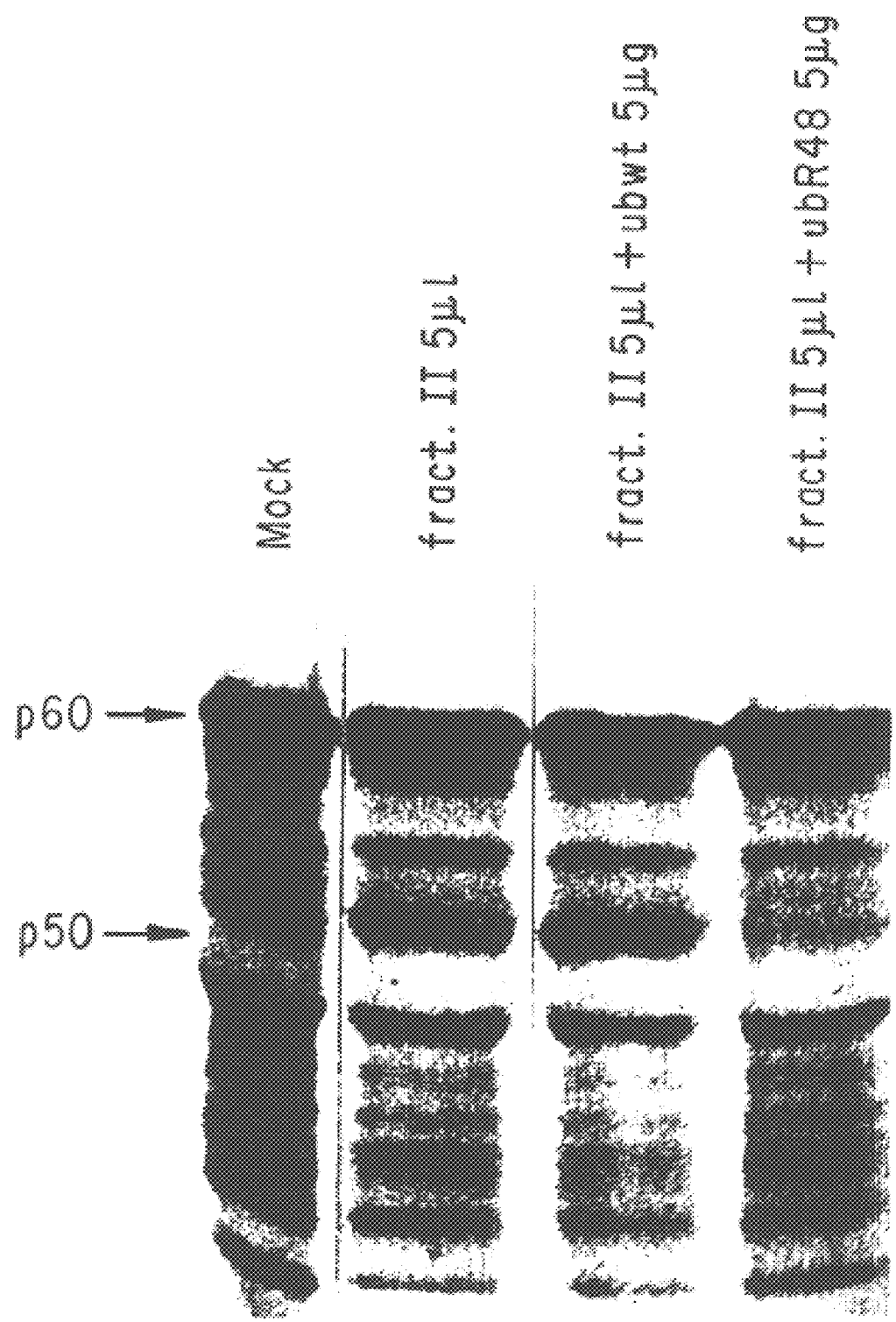

The results are shown in FIG. 7.

EXAMPLE 10

Processing of p105 in Saccharomyces cerevisiae Requires the Proteasome

Figure 8:
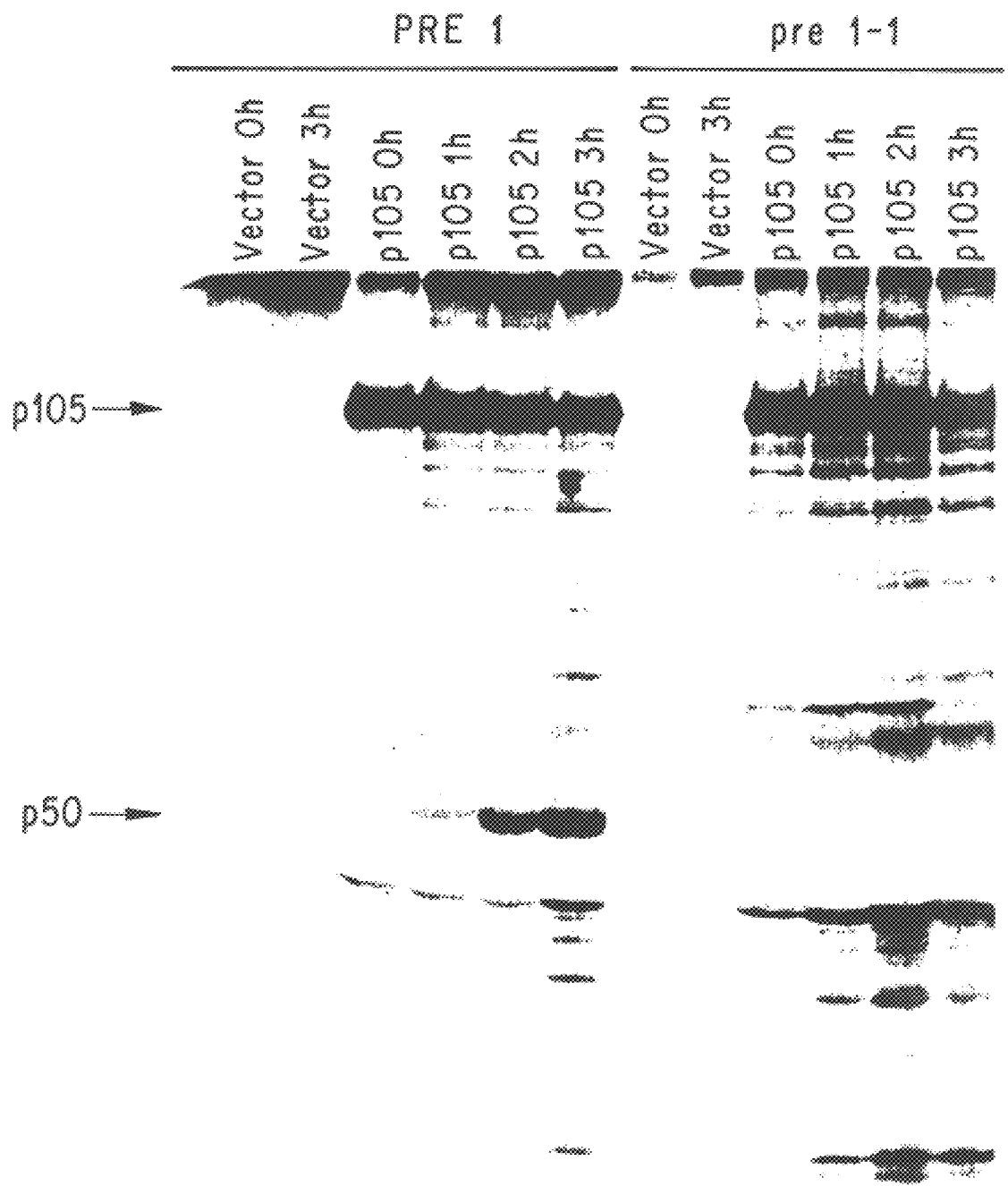
FIG. 8 shows that processing of p105 in *Saccharomyces cerevisiae* requires the proteasome.

Both wild-type (PRE 1) and proteasome mutant (pre1-1) yeast were transformed with human p105. The transformants were pulsed with $^{35}$S-methionine/cysteine for 20 minutes and chased with cold methionine/cysteine for various periods of time. Extracts were prepared, the lysates were immunoprecipitated with anti-p50 Ab and the proteins were resolved by SDS-PAGE. The results are shown in FIG. 8.

EXAMPLE 11

Specific Inhibitors of the Proteasome Block the Processing of p105 in vivo

Figure 9:
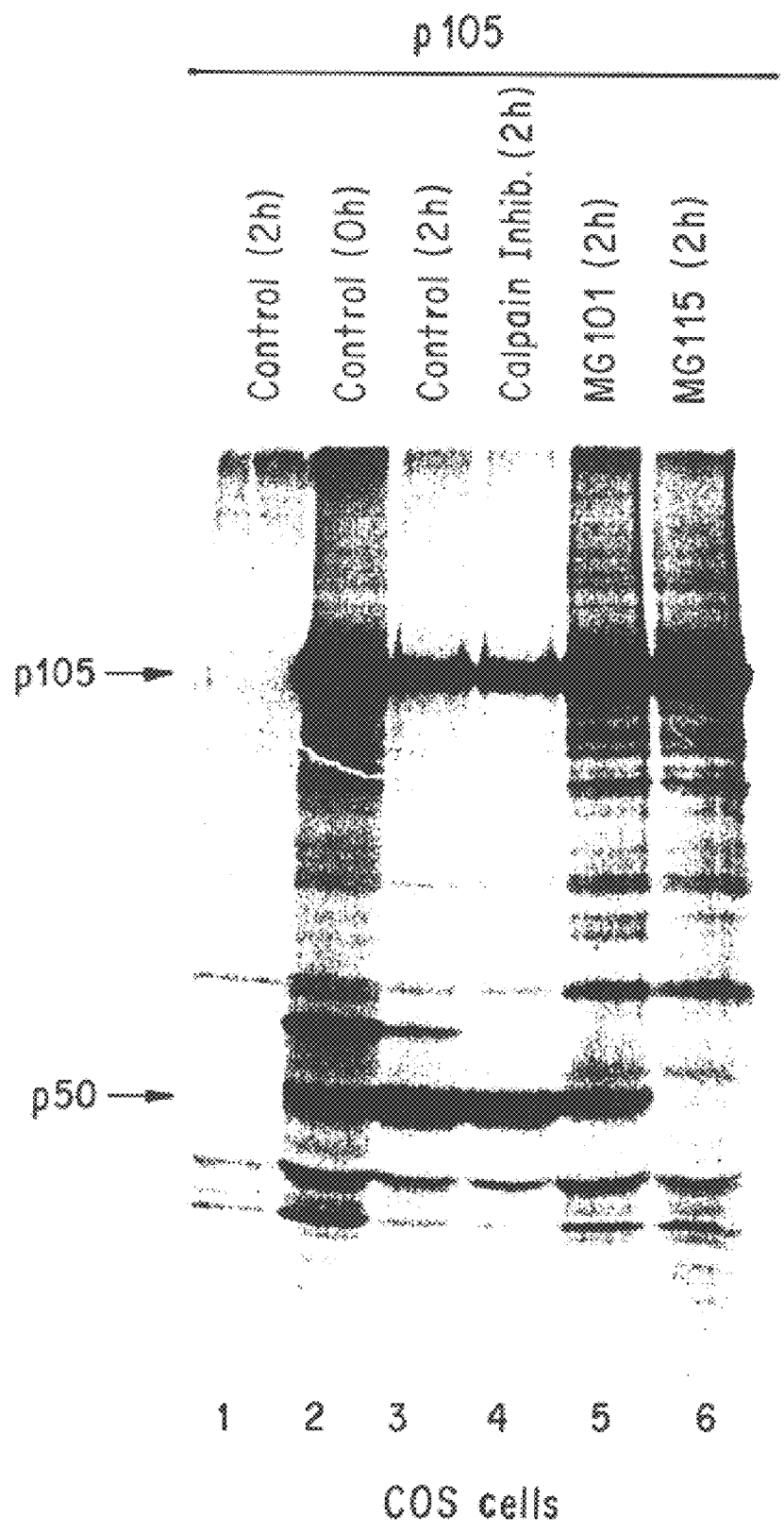
FIG. 9 shows that specific inhibitors of the proteasome block the processing of p105 in vivo.

COS cells were transfected with human p105. Inhibitors (Calpain inhibitor, MG101, and MG115) in 50 µM portions were added to the cells one hour prior to the addition of $^{35}$S-methionine/cysteine. A typical 20 minute pulse-2 hour chase experiment, immunoprecipitated with anti-p50 Ab followed by SDS-PAGE, is shown in FIG. 9. Only proteasome-specific inhibitors block p105 processing; non-specific protease inhibitors do not have an effect. These results were verified in vitro.

EXAMPLE 12

Specific Inhibitors of the Proteasome Block Activation of NF-κB

Figure 10:
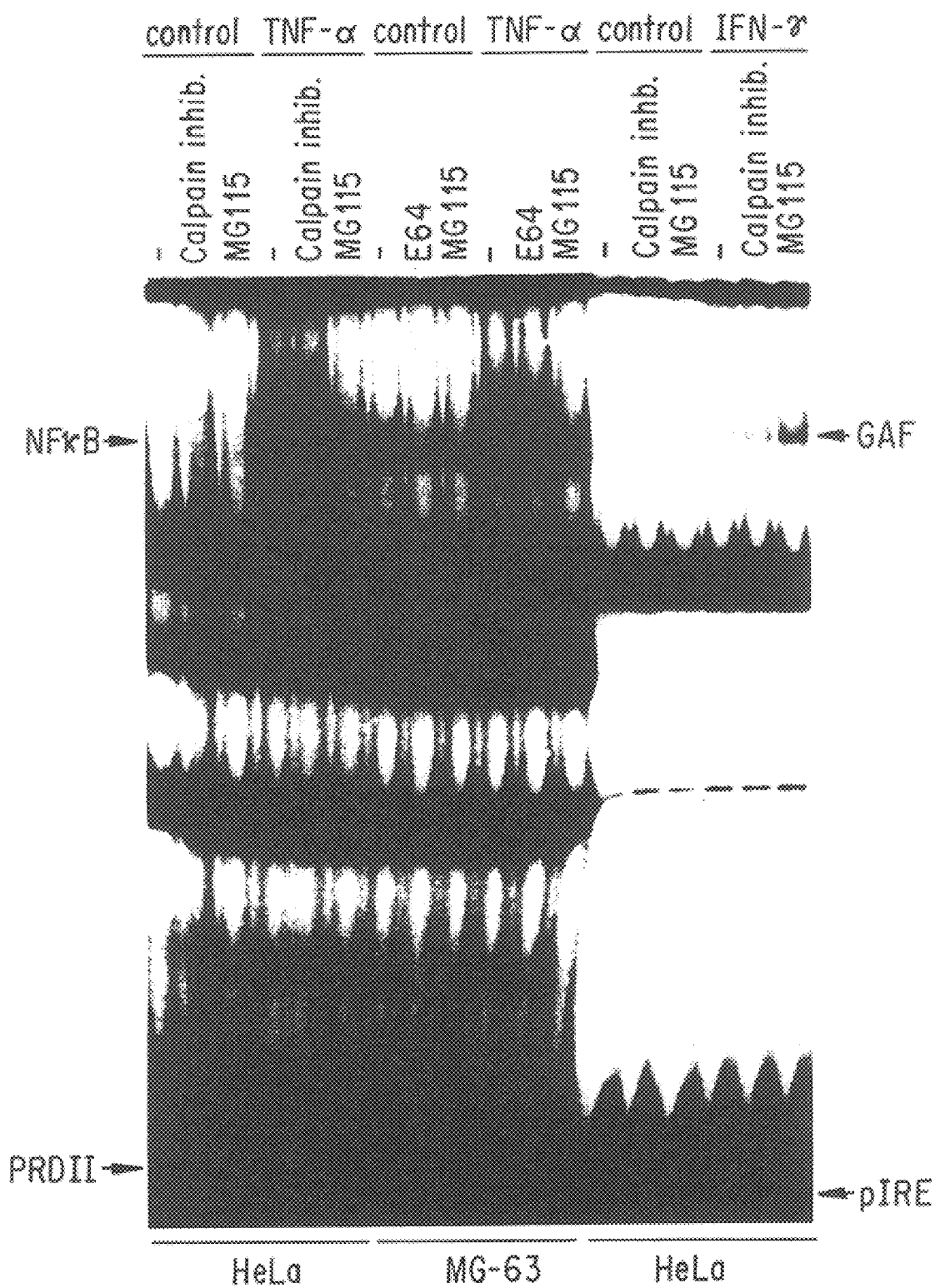
FIG. 10 shows that specific inhibitors of the proteasome block activation of NF-κB.

HeLa or MG63 cells were pretreated with inhibitors (50 μM) for one hour. Cells were then treated with TNF-α (1000 U/ml) or IFN-γ (1000 U/ml) for 30 and 60 minutes, respectively. Whole-cell extracts were prepared and analyzed by an electrophoretic mobility shift assay. The NF-κB site from the interferon-β gene was used to examine NF-κB binding activity and the pIRE site from the IRF-1 gene was used to measure gamma-activated factor (GAF) activity. The inhibitors only block NF-κB activation and have no effect on GAF induction. The results are shown in FIG. 10.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A method for treating a human with an inflammatory condition caused by NF-κB activity, said method comprising administering to the human a selective inhibitor of proteasome function or ubiquitin conjugation in an amount sufficient to reduce NF-κB activity.

2. The method of claim 1, wherein the inflammatory condition is characterized by elevated IL-6 or TNF-α levels.

3. A method for treating a human having an inflammatory condition comprising determining whether the human has elevated IL-6 or TNF-α levels and administering to the human a selective inhibitor of proteasome function or ubiquitin conjugation at a level sufficient to reduce NF-κB activity, whereby IL-6 or TNF-α levels are reduced.

* * * * *

UNITED STATES PATENT AND TRADEMARK OFFICE
CERTIFICATE OF CORRECTION

PATENT NO.   : 6,660,268 B1
DATED        : December 9, 2003
INVENTOR(S)  : Palombella et al.

It is certified that error appears in the above-identified patent and that said Letters Patent is hereby corrected as shown below:

<u>Title page,</u>
Item [73], Assignee, replace "Cambridge, PA" with -- Cambridge, MA --

Signed and Sealed this

Twenty-third Day of March, 2004

JON W. DUDAS
*Acting Director of the United States Patent and Trademark Office*